United States Patent
Yin et al.

(10) Patent No.: US 10,640,512 B2
(45) Date of Patent: May 5, 2020

(54) IMIDAZOPYRAZINAMINE PHENYL DERIVATIVE AND USE THEREOF

(71) Applicants: HANGZHOU SANYINTAI PHARMACEUTICAL TECHNOLOGY CO., LTD., Hangzhou, Zhejiang (CN); Jianming Yin, Lexington, MA (US)

(72) Inventors: Jianming Yin, Lexington, MA (US); Yubin Lv, Zhejiang (CN); Bangliang Li, Zhejiang (CN)

(73) Assignee: HANGZHOU SANYINTAI PHARMACEUTICAL TECHNOLOGY CO., LTD., Hangzhou, Zhejiang (CN)

( * ) Notice: Subject to any disclaimer, the term of this patent is extended or adjusted under 35 U.S.C. 154(b) by 0 days.

(21) Appl. No.: 16/311,979

(22) PCT Filed: Jun. 29, 2017

(86) PCT No.: PCT/CN2017/090908
§ 371 (c)(1),
(2) Date: Dec. 20, 2018

(87) PCT Pub. No.: WO2018/001331
PCT Pub. Date: Jan. 4, 2018

(65) Prior Publication Data
US 2019/0211023 A1 Jul. 11, 2019

(30) Foreign Application Priority Data

Jun. 30, 2016 (CN) .......................... 2016 1 0533291
Nov. 25, 2016 (CN) .......................... 2016 1 1062661

(51) Int. Cl.
C07D 487/04 (2006.01)
A61P 35/02 (2006.01)
A61P 11/06 (2006.01)
A61P 35/00 (2006.01)
A61P 3/10 (2006.01)
A61P 29/00 (2006.01)
A61P 37/08 (2006.01)
A61K 31/4985 (2006.01)
A61P 19/02 (2006.01)
A61P 19/04 (2006.01)

(52) U.S. Cl.
CPC ........ C07D 487/04 (2013.01); A61K 31/4985 (2013.01); A61P 3/10 (2018.01); A61P 11/06 (2018.01); A61P 19/02 (2018.01); A61P 19/04 (2018.01); A61P 29/00 (2018.01); A61P 35/00 (2018.01); A61P 35/02 (2018.01); A61P 37/08 (2018.01)

(58) Field of Classification Search
CPC .................................................... C07D 487/04
See application file for complete search history.

(56) References Cited

U.S. PATENT DOCUMENTS

2019/0367524 A1* 12/2019 Cai ...................... C07D 487/04

FOREIGN PATENT DOCUMENTS

| JP | 2010526768 A | 8/2010 |
| JP | 2014520866 A | 8/2014 |
| WO | 2008121742 A2 | 10/2008 |
| WO | 2013010380 A1 | 1/2013 |
| WO | 2013010868 A1 | 1/2013 |
| WO | 2015057992 A1 | 4/2015 |
| WO | 2016019237 A2 | 2/2016 |
| WO | 2016210165 A1 | 12/2016 |
| WO | 2017033113 A1 | 3/2017 |
| WO | 2017077507 A1 | 5/2017 |

OTHER PUBLICATIONS

Testa et al. Pure Appl. Chem. vol. 76, pp. 907-914 (2004). (Year: 2004).*
Norman, Expert Opinion on Investigational Drugs, vol. 25, No. 8, 891-899. (Year: 2016).*
English translation of International Search Report for International Application No. PCT/CN2017/090908, dated Oct. 12, 2017, 3 pages.
Examination Report issued in related Australian Application No. 2017287553 dated May 24, 2019, 3 pages.
Examination Report No. 2 for AU Application No. 2017287553, dated Sep. 17, 2019, 3 pages.
English translation of Japan Office Action dated Dec. 3, 2019 for related application 2018-569169; 5 pp.
Extended European Search Report for EP Application No. 17819328.0, dated Jan. 23, 2020, 11 pages.

* cited by examiner

*Primary Examiner* — Emily A Bernhardt
(74) *Attorney, Agent, or Firm* — Armstrong Teasdale LLP

(57) ABSTRACT

Imidazopyrazinamine phenyl derivatives, pharmaceutically acceptable salts and hydrates thereof, or metabolites thereof formed by any form of metabolism, and uses thereof in the preparation of medicaments for preventing and/or treating indications/diseases associated with BTK functions are disclosed. The disclosed imidazopyrazinamine phenyl derivatives are ideal high-efficient BTK inhibitors for treating or preventing diseases such as rheumatoid arthritis, B cell lymphoma, leukemia, multiple myeloma, allergies, asthma, multiple sclerosis, type I diabetes and systemic lupus erythematosus.

6 Claims, No Drawings

IMIDAZOPYRAZINAMINE PHENYL DERIVATIVE AND USE THEREOF

CROSS-REFERENCE TO RELATED APPLICATIONS

This application is a U.S. National Phase Application of PCT/CN2017/090908, filed Jun. 29, 2017, which claims the benefit of priority to CN Application No. 201610533291.X, filed Jun. 30, 2016, and CN Application No. 201611062661.2, filed Nov. 25, 2016, the contents of which are hereby expressly incorporated by reference in their entirety.

TECHNICAL FIELD

The present invention relates to an imidazopyrazinamine phenyl derivative, and use thereof in the preparation of medicaments for preventing and/or treating indications/diseases associated with BTK functions.

TECHNICAL BACKGROUND

Bruton's Tyrosine Kinase (BTK) is a member of the tyrosine kinase TEC family and plays an important role in B cell activation and cell transduction. B cell receptor (BCR) is a key regulatory site for B cell activity, abnormal signaling can cause dysregulated B cell proliferation and the formation of pathogenic autoantibodies, leading to a variety of autoimmune diseases and inflammatory diseases.

BTK is located at the membrane-proximal section and immediately downstream of BCR, BTK deficiency can block BCR signaling. Thus, an effective therapeutic approach to block B cell mediated diseases can be provided by inhibiting BTK. BTK inhibitors can be used in the treatment of diseases such as rheumatoid arthritis, B cell lymphoma, leukemia, multiple myeloma, allergies, asthma, multiple sclerosis, type I diabetes and systemic lupus erythematosus. Currently, two BTK inhibitors being developed extensively are ibrutinib and ACP-196 (acalabrutinib). The former was approved by FDA in 2013 for the treatment of mantle cell lymphoma (MCL) and chronic lymphocytic leukemia (CLL). The latter is currently in phase III clinical trials.

Both BTK inhibitors have some toxic side effects, such as: thrombocytopenia, decreased hemoglobin, diarrhea, neutropenia, anemia, fatigue, headache, musculoskeletal pain, angioedema, upper respiratory tract infection, nausea, bruising, dyspnea, constipation, rash, arthralgia, bellyache, vomiting and loss of appetite etc. In the two inhibitors, the toxic side effects of ibrutinib are much larger than those of ACP-196 (Acalabrutinib (ACP-196) in Relapsed Chronic Lymphocytic Leukemia (The New England Journal of Medicine, 374; 4, 2016)).

These toxic side effects are caused by the low selectivities to the kinase and the long half lives of the drugs.

In literature: Acalabrutinib (ACP-196) in Relapsed Chronic Lymphocytic Leukemia (The New England Journal of Medicine, 374; 4, 2016), it is disclosed that three kinases, EGFR/ITK/TEC are clearly related to side effects.

In a conference paper: Presented at the 2nd International Conference on New Concepts in B-cell Malignancies; 9-11 Sep. 2016; Estoril, Portugal, it is disclosed that the half life of ibrutinib was 6 hours and the half life of ACP-196 was 1.13 hours.

SUMMARY OF THE INVENTION

The technical problem to be solved by the present invention is to provide a novel imidazopyrazinamine phenyl derivative which has relative low toxic side effects and is an ideal non-reversible BTK inhibitor.

The present invention also provides the use of an imidazopyrazinamine phenyl derivative, a pharmaceutically acceptable salt, hydrate thereof, or a metabolite thereof formed by any form of metabolism for the preparation of medicaments for preventing and/or treating indications/diseases associated with BTK functions.

In order to solve the above technical problems, the present invention adopts the following technical solutions:

An objective of the present invention is to provide an imidazopyrazinamine phenyl derivative having a structure represented by general formula (I), a pharmaceutically acceptable salt and hydrate thereof, or a metabolite thereof formed by any form of metabolism,

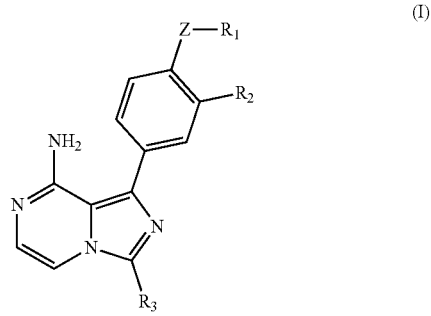

wherein: Z is selected from NH, C=O or O;
$R_1$ is an aromatic ring, a five-membered heteroaromatic ring or a six-membered heteroaromatic ring, which is optionally substituted with 0-5 C1-C4 alkyls or halogens independently; $R_2$ is H, C1-C4 alkyl or halogen;
$R_3$ is

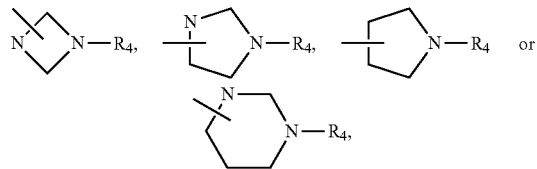

wherein $R_4$ is C(O)C≡CR$_5$ or C(O)CH=CHR$_5$, and $R_5$ is H or C1-C4 alkyl.

In the present invention, in the imidazopyrazinamine phenyl derivative having the structure represented by general formula (I), a pharmaceutically acceptable salt and hydrate thereof, or a metabolite thereof formed by any form of metabolism, non-exchangeable hydrogen is not substituted, or is partially or completely substituted with deuterium.

Preferably, $R_1$ is a benzene ring, a six-membered heteroaromatic ring containing 1 or 2 nitrogens, which is optionally substituted with 0-2 C1-C4 alkyls.

Further preferably, $R_1$ is

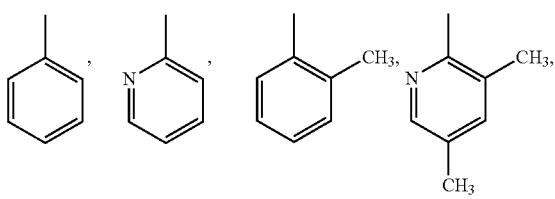

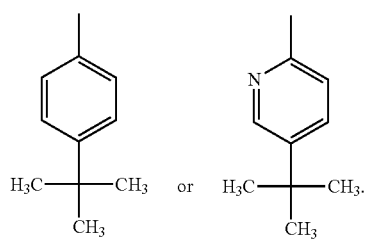
Preferably, R₂ is H, methyl, ethyl, n-propyl, isopropyl, n-butyl, isobutyl, sec-butyl or tert-butyl.
Preferably, $R_3$ is
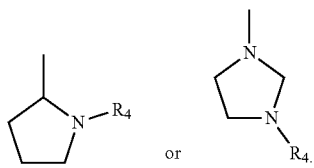
Preferably, $R_5$ is H, methyl, ethyl, n-propyl, isopropyl, n-butyl, isobutyl, sec-butyl or tert-butyl. Specifically, the imidazopyrazinamine phenyl derivative is one of the compounds represented by the following structural formulas:
(I-1)
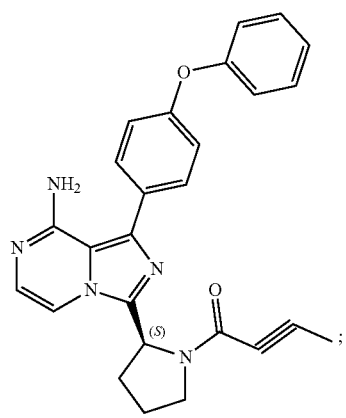
(I-2)
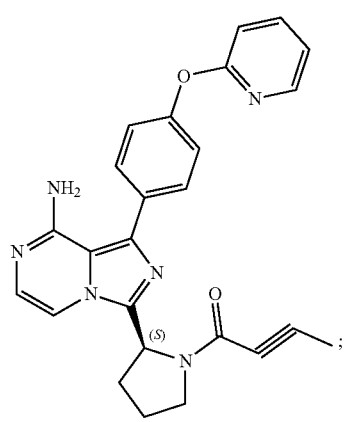
(I-3)
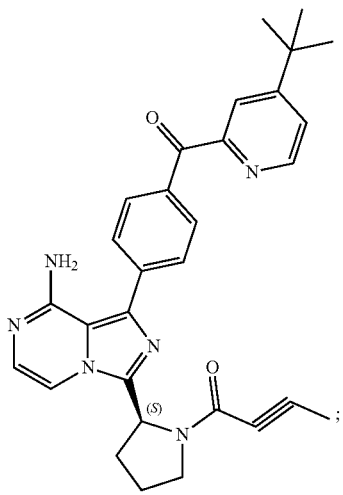
(I-4)
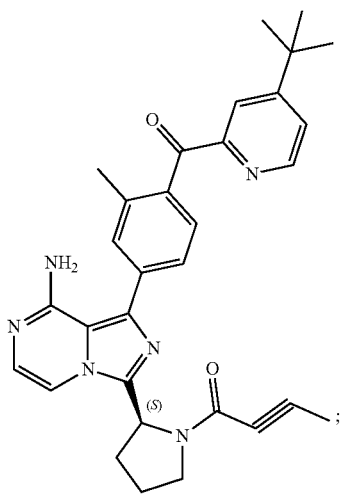
(I-5)
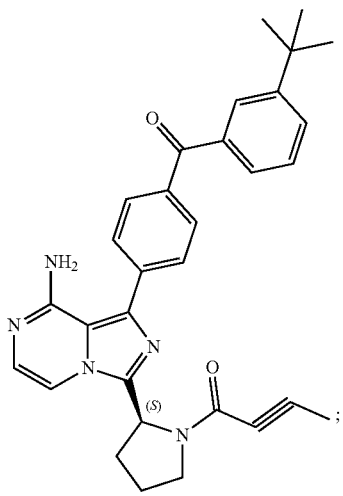

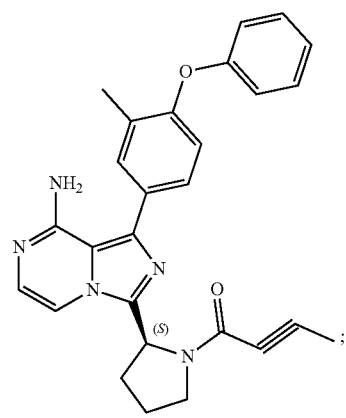
(I-6)
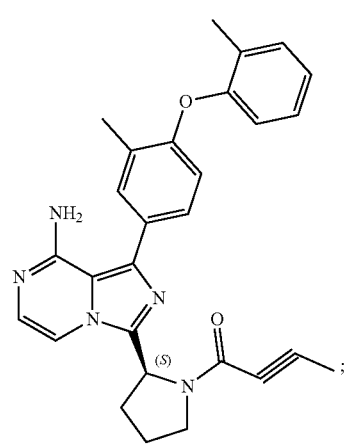
(I-7)
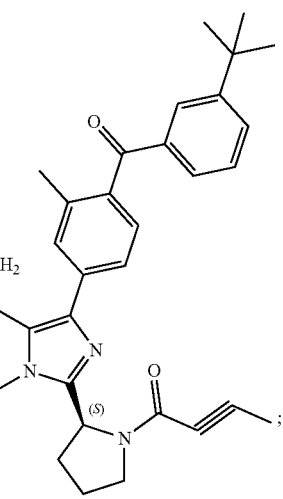
(I-8)
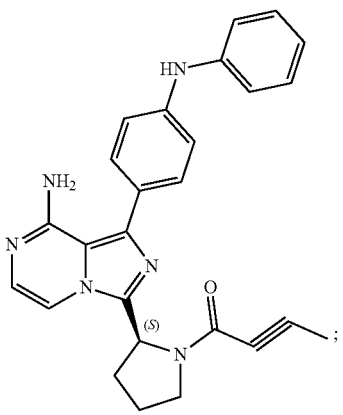
(I-9)
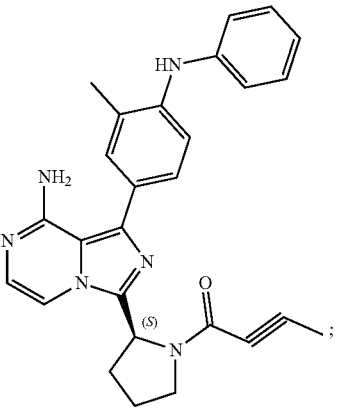
(I-10)
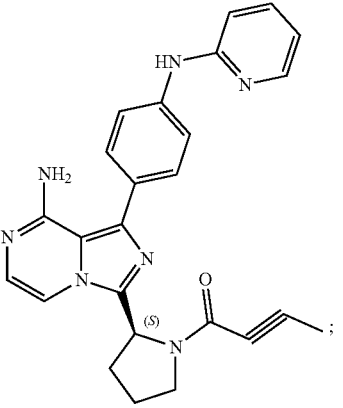
(I-11)
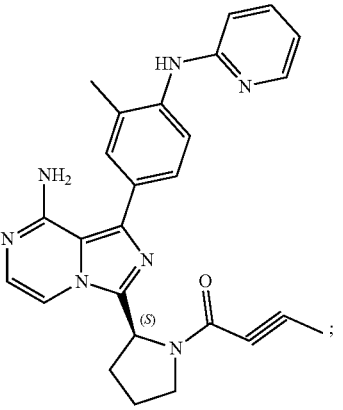
(I-12)

(I-13)
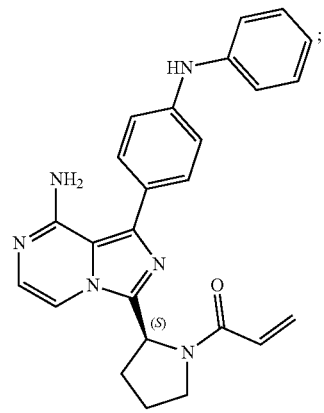
(I-14)
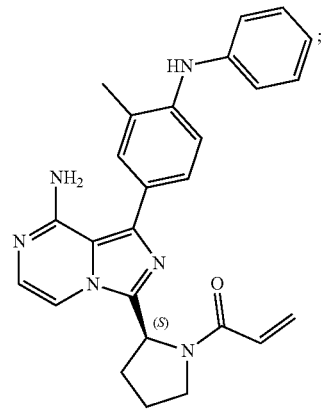
(I-15)
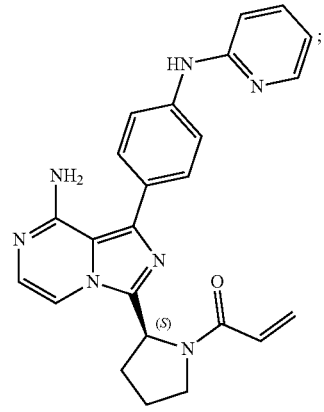
(I-16)
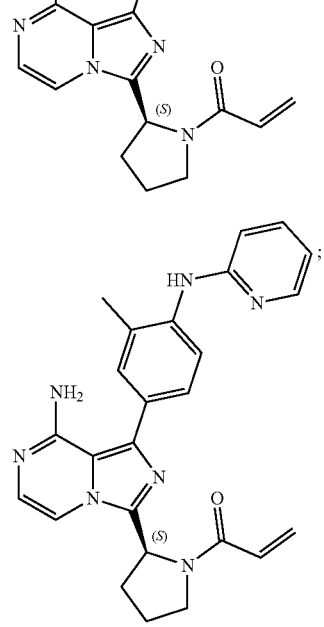
(I-17)
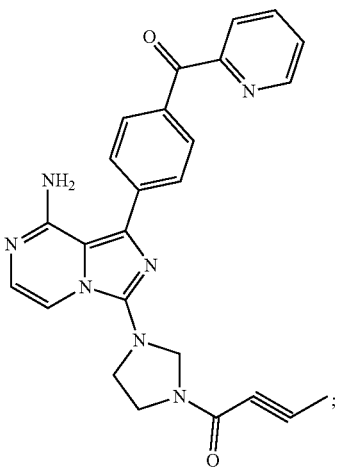
(I-18)
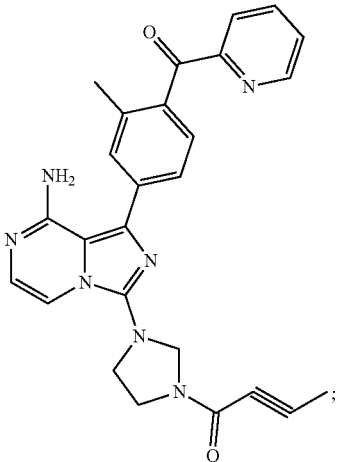
(I-19)
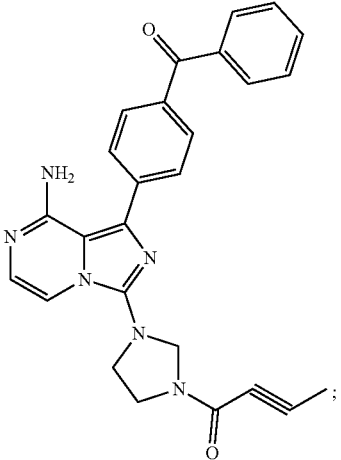

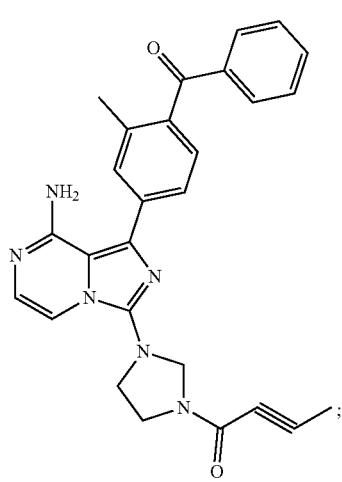
(I-20)
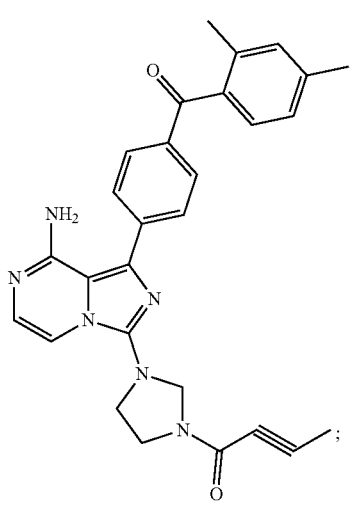
(I-23)
(I-21)
(I-24)
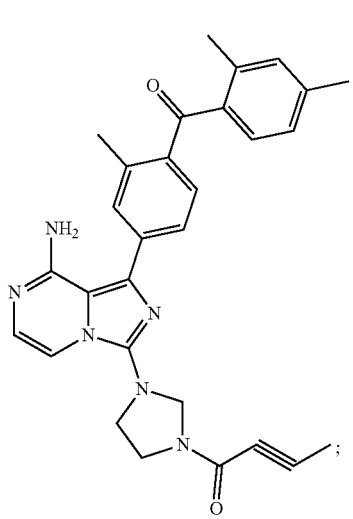
(I-22)
(I-25)
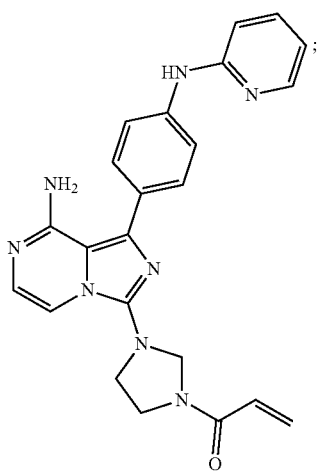

-continued
(I-26)
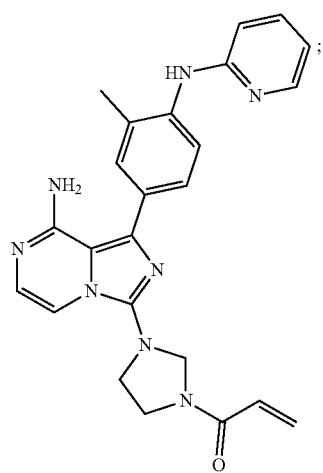
(I-29)
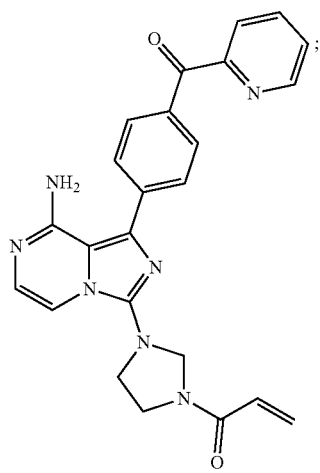
(I-27)
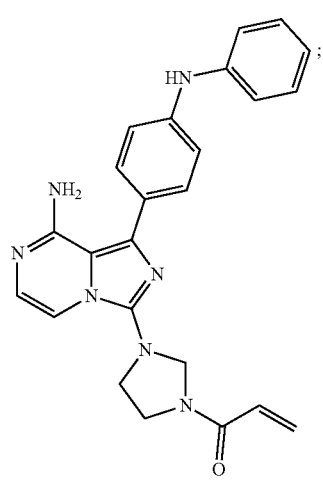
(I-30)
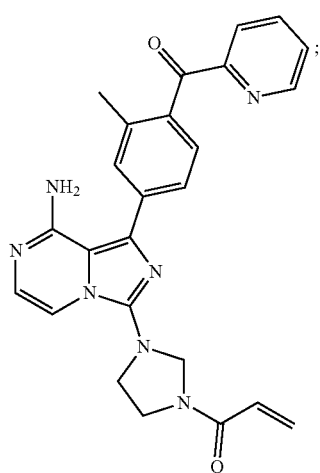
(I-28)
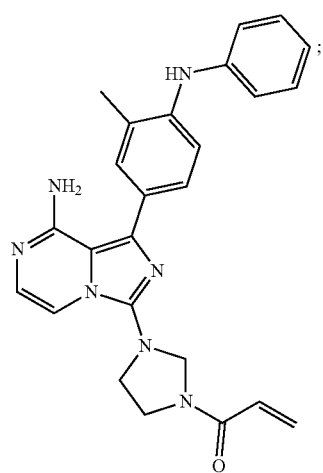
(I-31)
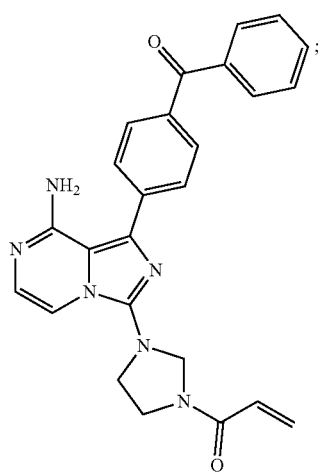

(I-32)
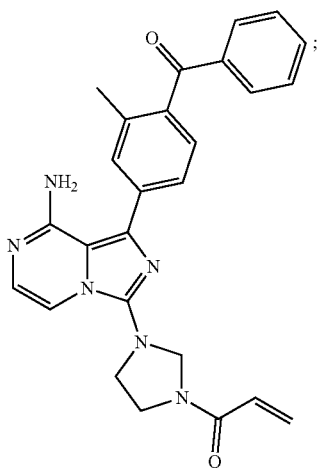

(I-33)
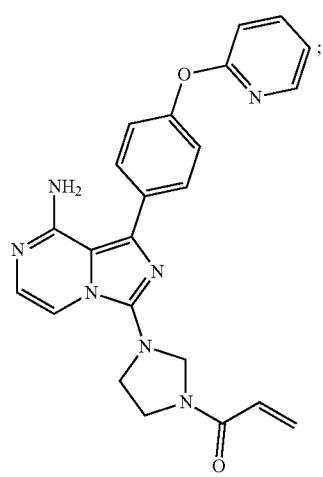

(I-34)
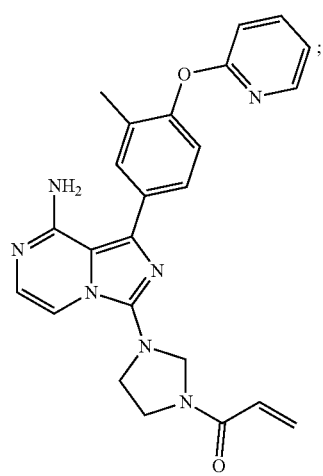

(I-35)
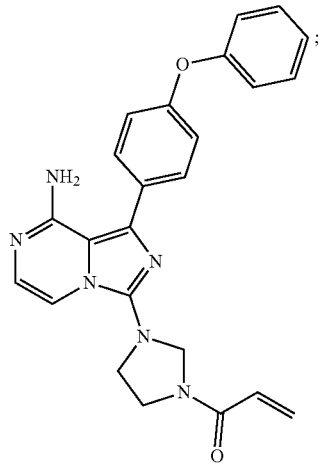

(I-36)
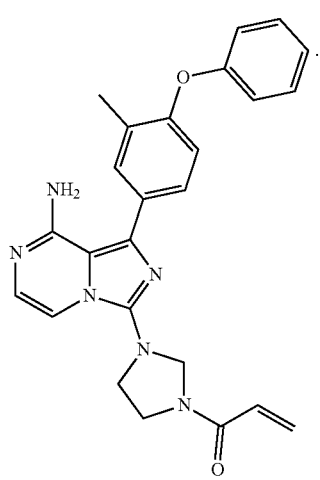

Another objective of the present invention is to provide an imidazopyrazinamine phenyl derivative having a structure represented by general formula (II), a pharmaceutically acceptable salt and hydrate thereof, or a metabolite thereof formed by any form of metabolism, (II)
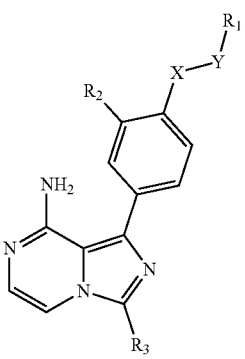

wherein:
one of X and Y is NH and the other is C═O;
$R_1$ is an aromatic ring, a five-membered heteroaromatic ring or a six-membered heteroaromatic ring, which is optionally substituted with 0-5 C1-C4 alkyls or halogens independently;

R₂ is H, C1-C4 alkyl or halogen;
R₃ is

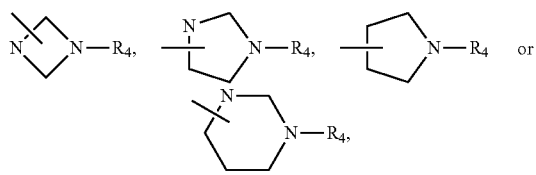

wherein R₄ is C(O)C≡CR₅ or C(O)CH=CHR₅, and R₅ is H or C1-C4 alkyl;
wherein when X is C=O, Y is NH, R₃ is

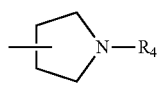

and R₁ is a five-membered heteroaromatic ring or a six-membered heteroaromatic ring, R₂ is C1-C4 alkyl.

In the present invention, in the imidazopyrazinamine phenyl derivative having the structure represented by general formula (II), a pharmaceutically acceptable salt and hydrate thereof, or a metabolite thereof formed by any form of metabolism, non-exchangeable hydrogen is not substituted, or is partially or completely substituted with deuterium.

Preferably, R₁ is a benzene ring, a six-membered heteroaromatic ring containing 1 or 2 nitrogens, which is optionally substituted with 0-2 C1-C4 alkyls.

Further preferably, R₁ is

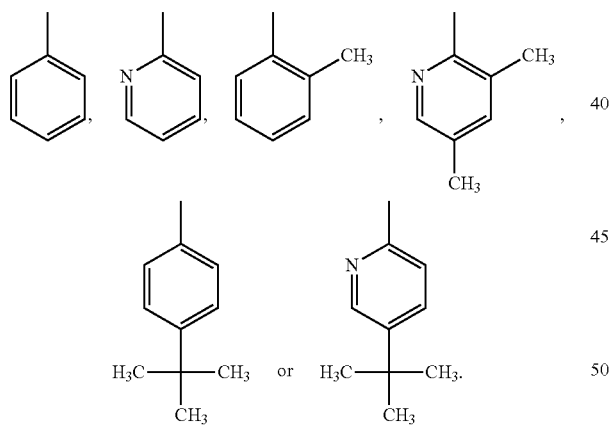

Preferably, R₂ is H, methyl, ethyl, n-propyl, isopropyl, n-butyl, isobutyl, sec-butyl or tert-butyl.
Preferably, R₃ is

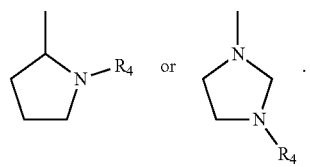

Preferably, R₅ is H, methyl, ethyl, n-propyl, isopropyl, n-butyl, isobutyl, sec-butyl or tert-butyl. Specifically, the imidazopyrazinamine phenyl derivative is one of the compounds represented by the following structural formulas:

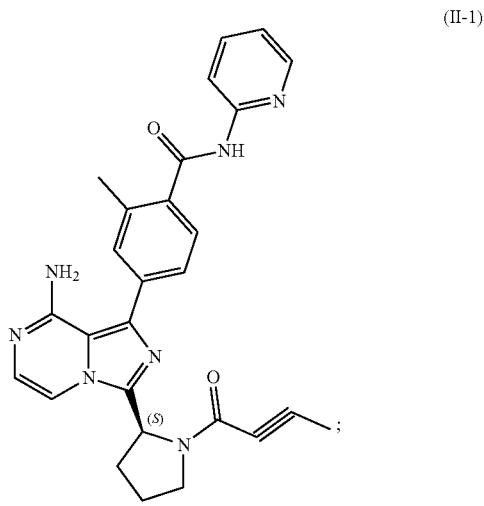

(II-1)

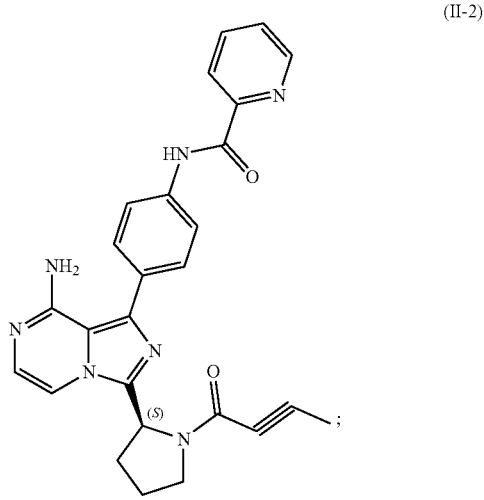

(II-2)

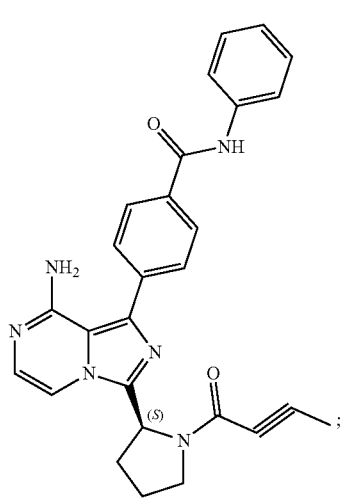

(II-3)

(II-4)
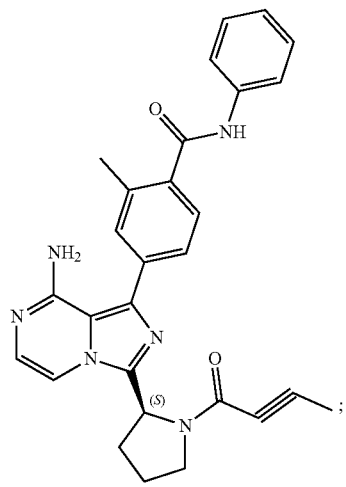
(II-5)
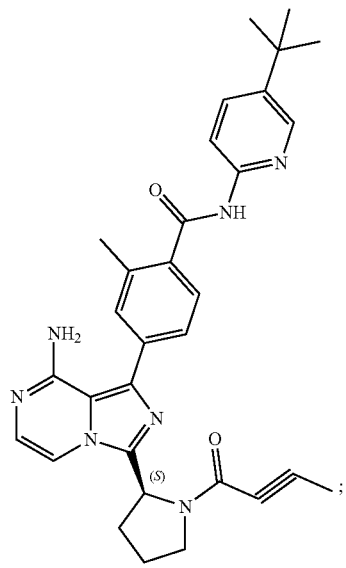
(II-6)
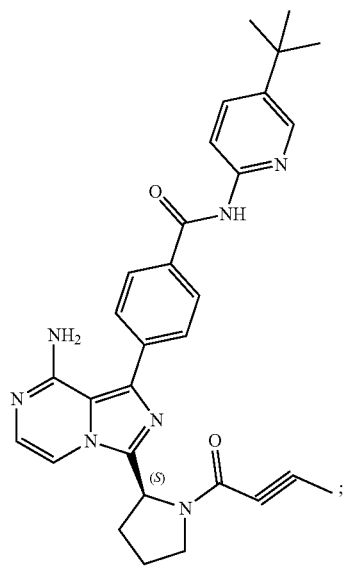
(II-7)
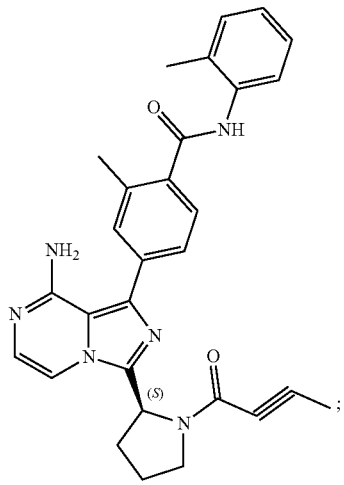
(II-8)
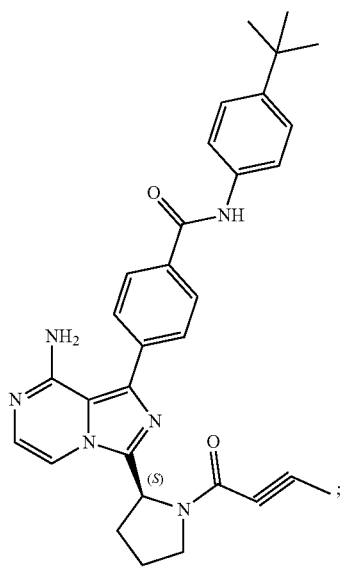
(II-9)
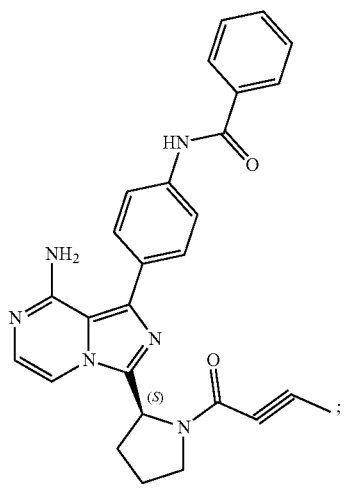

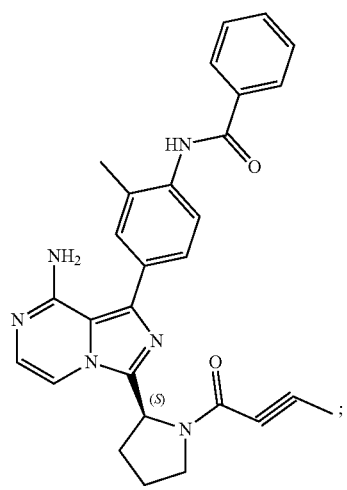
(II-10)
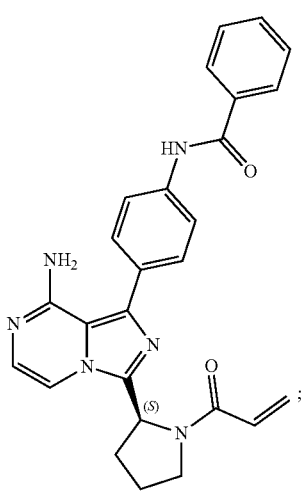
(II-13)
(II-11)
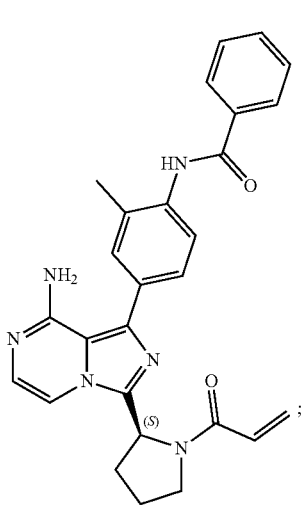
(II-14)
(II-12)
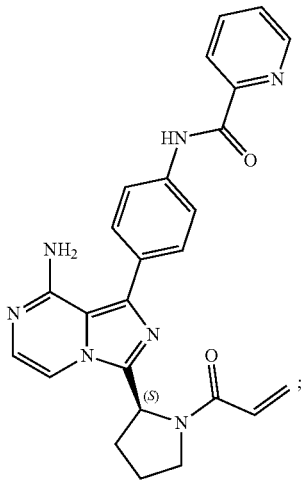
(II-15)

(II-16)
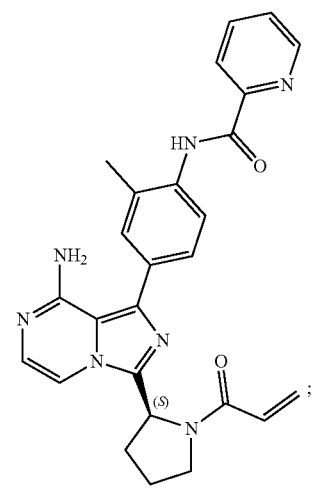
(II-17)
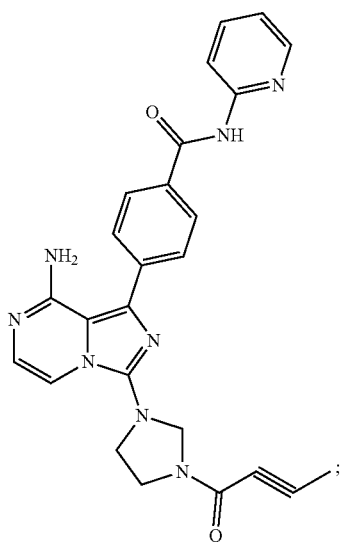
(II-18)
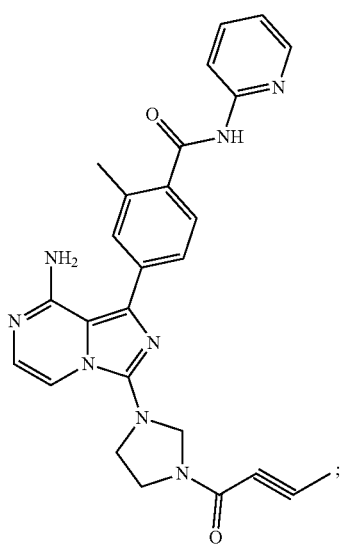
(II-19)
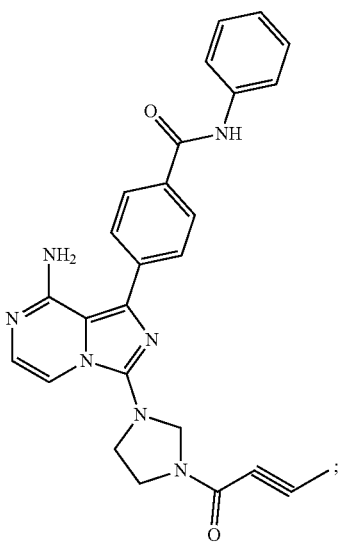
(II-20)
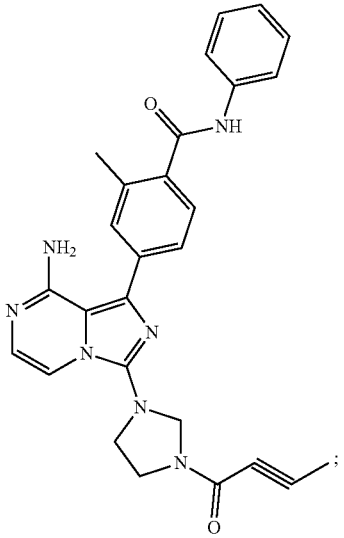
(II-21)
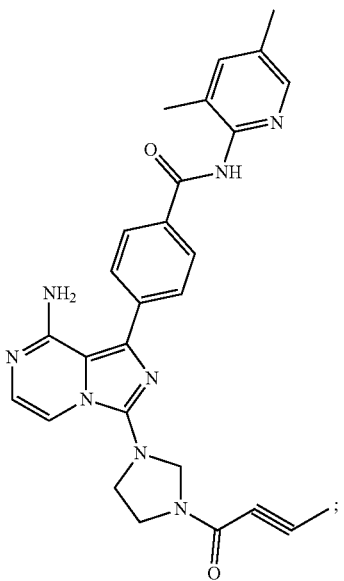

(II-22)
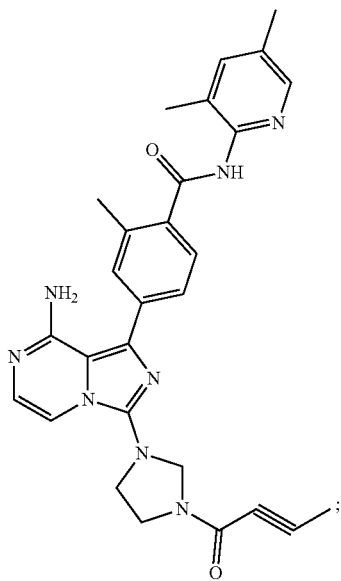
(II-23)
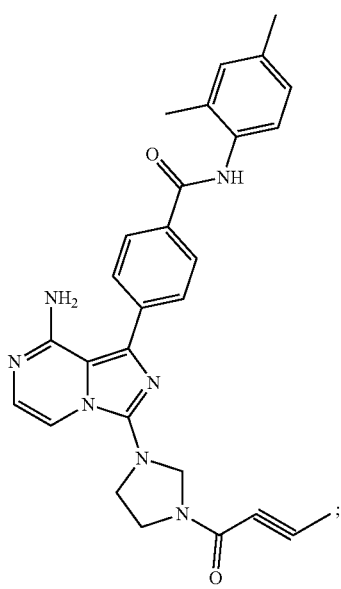
(II-24)
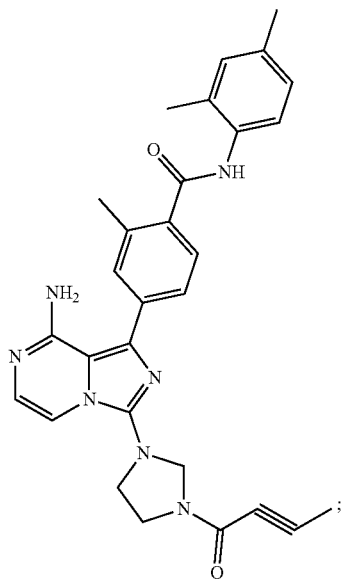
(II-25)
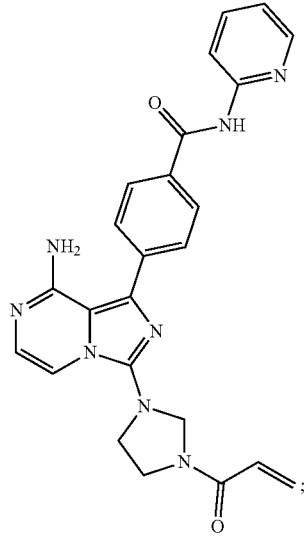
(II-26)
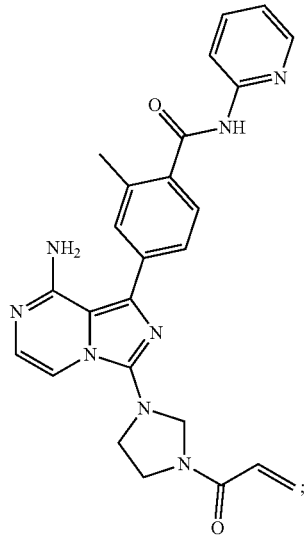

-continued
(II-27)
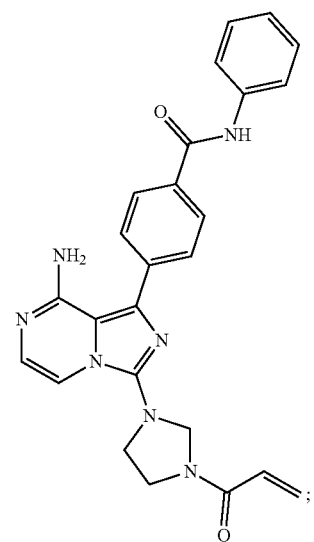
(II-28)
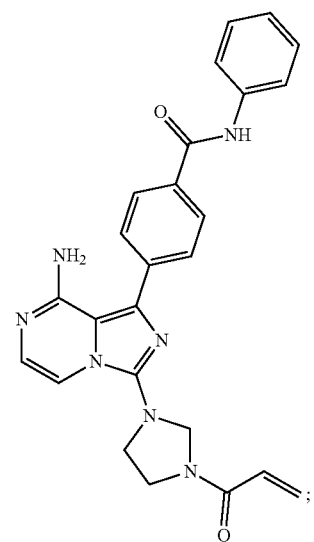
(II-29)
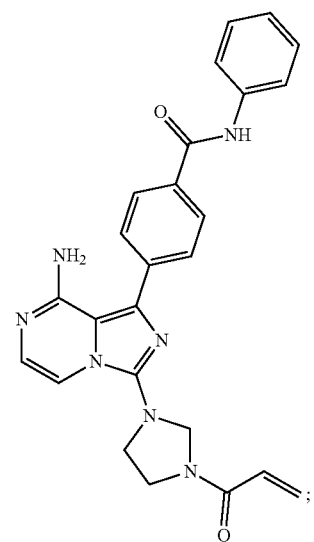
(II-30)
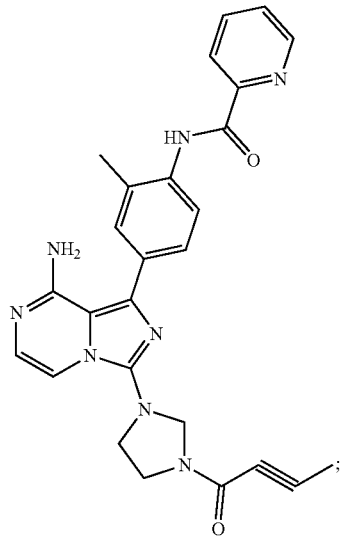
(II-31)
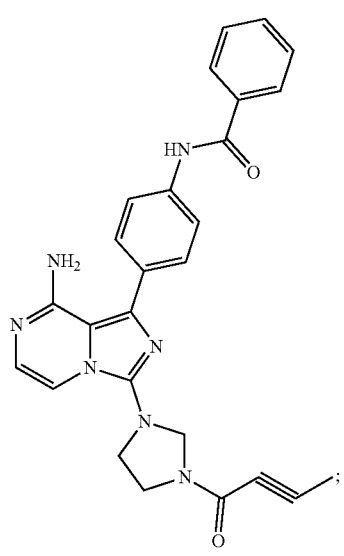
(II-32)
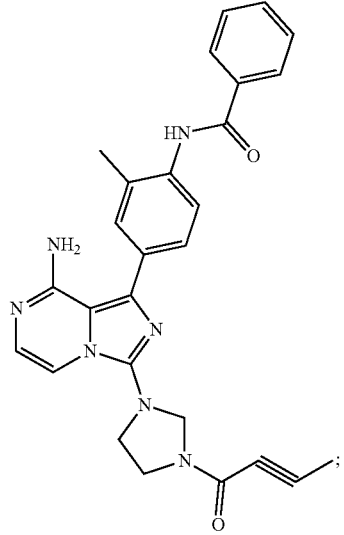

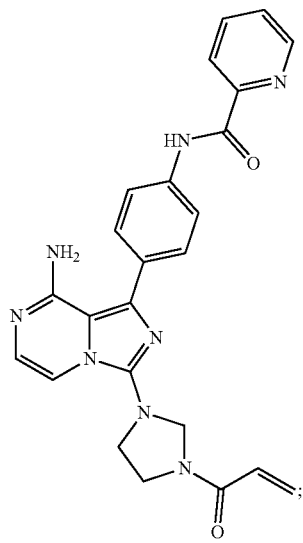

(II-33)

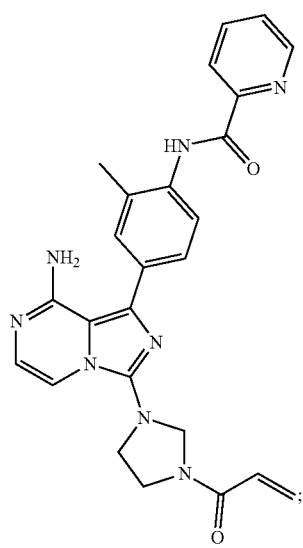

(II-34)

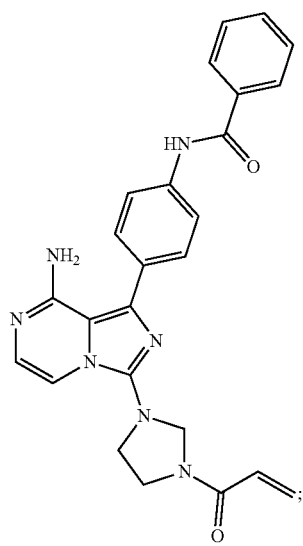

(II-35)

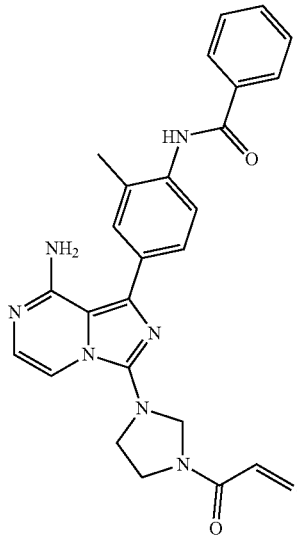

(II-36)

According to the present invention, the imidazopyrazinamine phenyl derivative can be not only a single compound but also a mixture of a plurality of compounds satisfying the requirements of general formula (I) or general formula (II), and a different isomer of the same compound such as a racemate, a enantiomer, a diastereomer and the like. The pharmaceutically acceptable salt can be, but is not limited to hydrochloride, phosphate, sulfate, acetate, maleate, mesylate, besylate, benzoate, toluenesulfonate, succinate, fumarate, tartrate, gallate, citrate and the like. The prodrug of a compound having general formula (I) or general formula (II) refers to a substance which can be converted into at least one compound of structure formula (I) or structure formula (II) or a salt thereof by metabolism or chemical reaction in a subject when administered using a suitable method.

The preparation of the imidazopyrazinamine phenyl derivative of the invention can be carried out by synthesis routes in analogous methods well known in the field of chemistry, especially the compounds of the present invention can be synthesized in accordance with the description contained herein. Reagents are generally obtained from commercial sources or are readily prepared using methods well known to those skilled in the art.

In the present invention, an aromatic ring refers to a conjugated planar ring system, wherein the bonds between atoms are not discontinuous alternating single and double bonds, the aromatic ring is an organic aromatic compound covered by a delocalized π electron cloud, having only carbon element in the ring. Five-membered heteroaromatic ring and six-membered heteroaromatic ring refer to aromatic rings having non-carbon element in the ring.

The third objective of the present invention is to provide use of an imidazopyrazinamine phenyl derivative having general formula (I) as described, a pharmaceutically acceptable salt and hydrate thereof, or a metabolite thereof formed by any form of metabolism or an imidazopyrazinamine phenyl derivative having general formula (II) as described, a pharmaceutically acceptable salt and hydrate thereof, or a metabolite thereof formed by any form of metabolism, for the preparation of medicaments for preventing and/or treating indications/diseases associated with BTK functions. Specifically, the indication associated with BTK functions can be diseases such as rheumatoid arthritis, B cell lymphoma, leukemia, multiple myeloma, allergies, asthma, multiple sclerosis, type I diabetes and systemic lupus erythematosus etc.

The fourth objective of the present invention is to provide an intermediate, for the preparation of the imidazopyrazinamine phenyl derivative having general formula (I) as described, the pharmaceutically acceptable salt and hydrate thereof, or the metabolite thereof formed by any form of metabolism, or of the imidazopyrazinamine phenyl derivative having general formula (II) as described, the pharmaceutically acceptable salt and hydrate thereof, or the metabolite thereof formed by any form of metabolism, the general structural formula of the intermediate is:

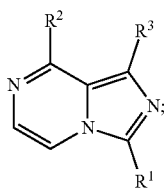

wherein, $R^1$ is

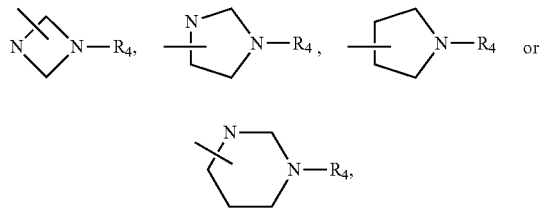

$R_4$ is a nitrogen protecting group or H;
$R^2$ is halogen or $NH_2$;
$R^3$ is

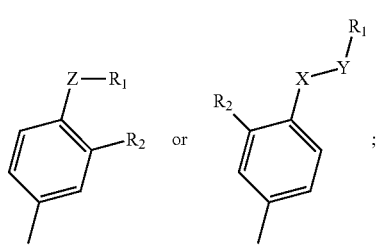

Z is selected from NH, C=O or O; X is NH and Y is C=O;
$R_1$ is an aromatic ring, a five-membered heteroaromatic ring or a six-membered heteroaromatic ring, which is optionally substituted with 0-5 C1-C4 alkyls or halogens independently; $R_2$ is H, C1-C4 alkyl or halogen.

Preferably, the nitrogen protecting group is a benzyloxycarbonyl group.

Preferably, the halogen in $R^2$ is Cl.

Specifically, the intermediate is one of the following structural formulas:

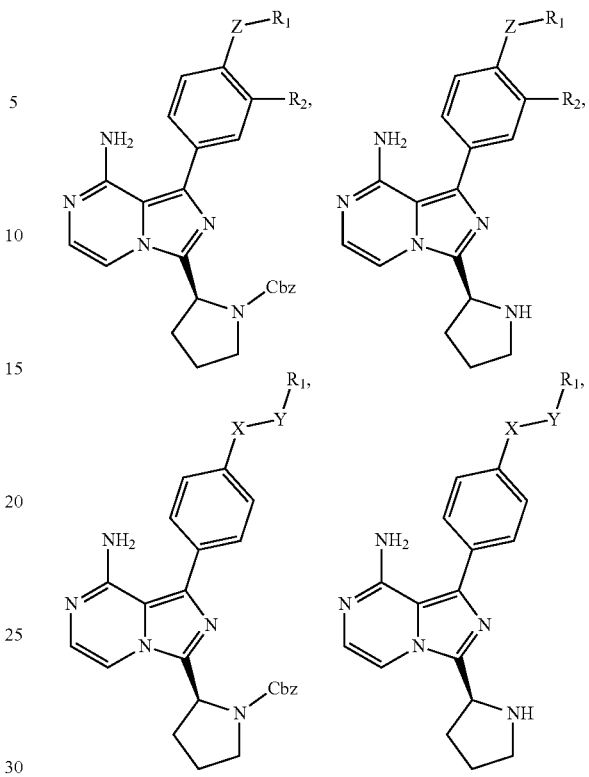

wherein Z is selected from NH, C=O or O;
X is NH and Y is C=O;
$R_1$ is an aromatic ring, a five-membered heteroaromatic ring or a six-membered heteroaromatic ring, which is optionally substituted with 0-5 C1-C4 alkyls or halogens independently;
$R_2$ is H, C1-C4 alkyl or halogen.

Due to the implementation of the above technical solutions, the present invention has the following advantages compared with the prior art:

the compounds provided by the present invention are novel imidazopyrazinamine phenyl derivatives which are ideal high efficient BTK inhibitors and which provide an effective therapeutic approach to block B cell mediated diseases by inhibiting BTK. The compounds of the present invention have novel structures, high activities, good pharmacokinetic properties and high oral bioavailabilities. The compounds of the present invention have high kinase selectivities, weak or no irreversible inhibitions of related kinases, decreasing the resulting adverse effects. Meanwhile, faster metabolism rates and short half-lives can avoid the risks of immune side reactions due to excessive inhibition of BTK. Further, the plasma peak concentration time ($T_{max}$) of the compounds of the present invention after oral administration is small, the peak plasma concentration can be reached very quickly, so that the drug takes effect very fast. Thus, the compounds of the present invention can be used in the preparation of medicaments for treating or preventing various indications associated with BTK functions and having lower side effects.

EMBODIMENTS

The present invention will be further described in detail with reference to specific embodiments, but the present invention is not limited to the following examples.

Example 1
The compound of formula Ia, i.e, the above (II-2), having a chemical structure as shown below:
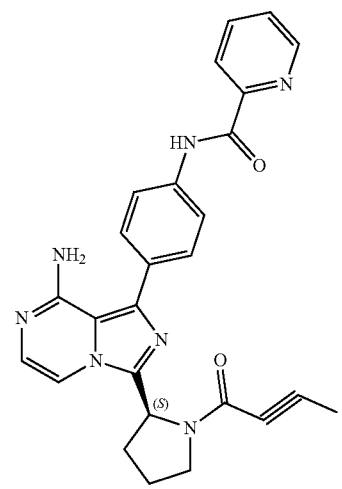
the compound of formula Ia can be obtained by the following synthesis route:
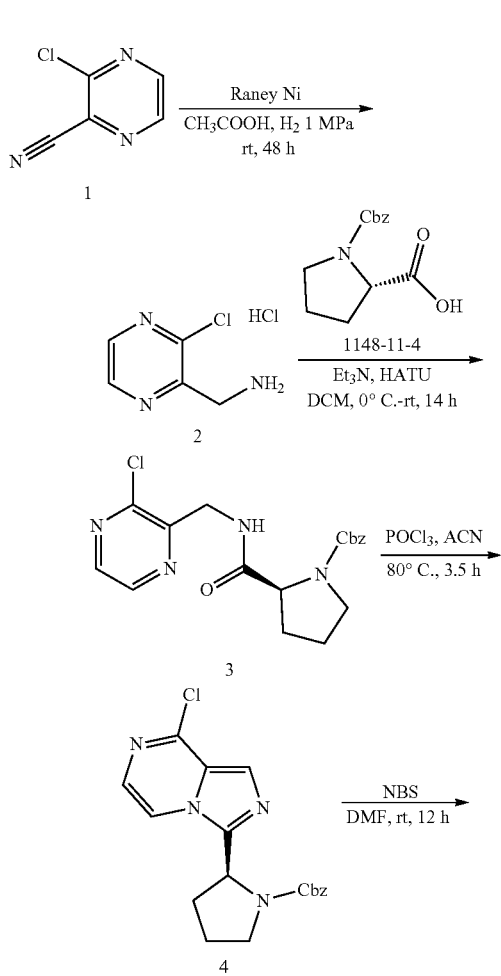
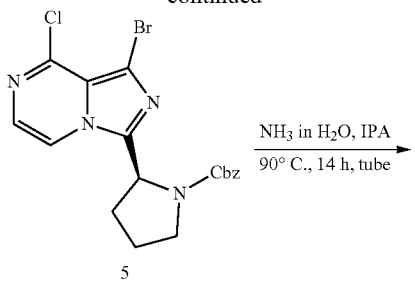
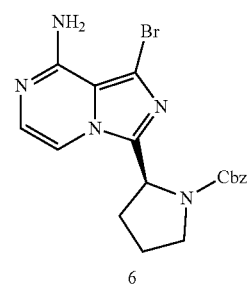
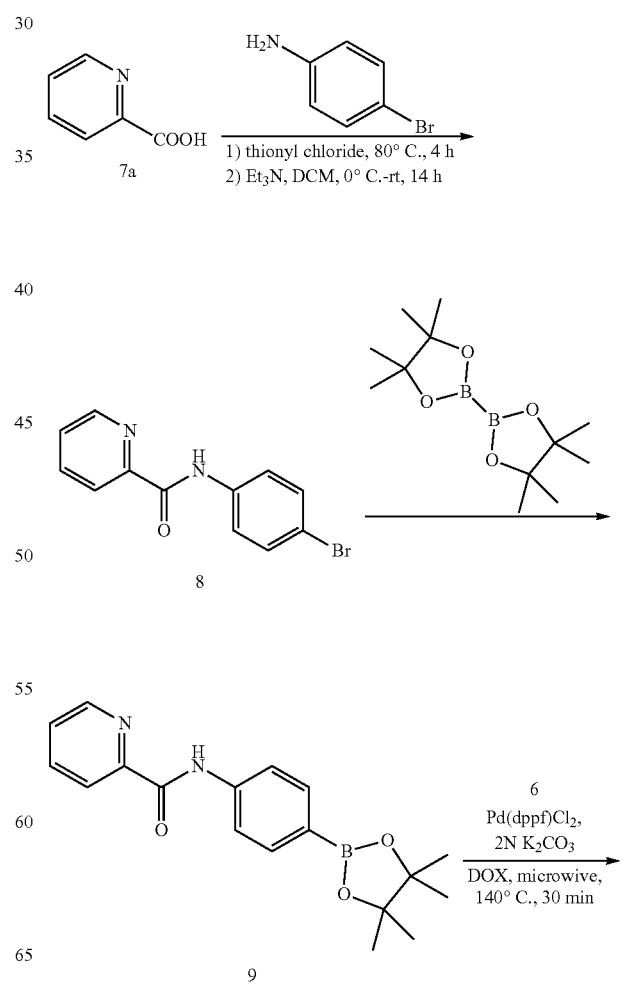

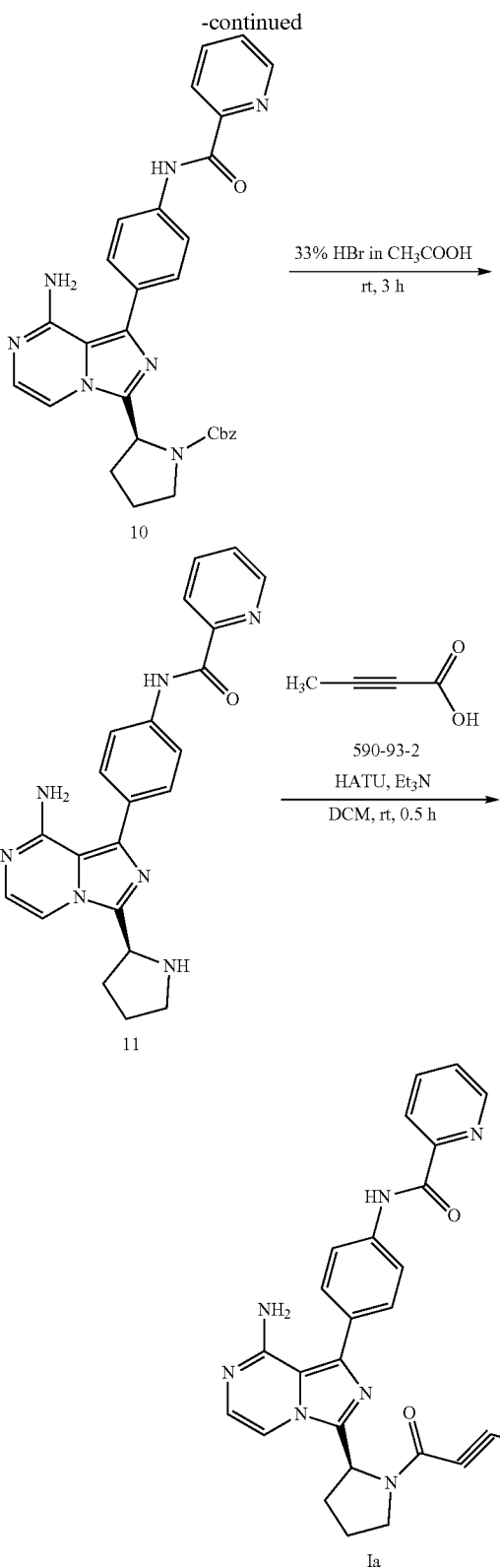

the preparation method of the compound of formula Ia specifically comprises the following steps:

(1) preparation of intermediate 2: compound 1 (90 g, 645 mmol), CH₃COOH (1 L) and Raney Ni (20 g) were added to a 2 L autoclave successively. A reaction was carried out in the autoclave while the reaction solution was stirred under a hydrogen pressure of 1 MPa for 48 hours at atmospheric temperature. After the reaction was completed, the reaction solution was filtered through diatomite, and a solution of HCl in MeOH (200 mL, 6.0N) was used to wash diatomite. The filtrate after being concentrated was poured into toluene and the obtained system was stirred, and was then concentrated again. The obtained mixture was stirred in MTBE (methyl tert-butyl ether) and was filtered. The filter cake was stirred in MTBE and MeOH and was then filtered to obtain intermediate 2 (40 g, yield: 35%) as a brown solid. LCMS showed a molecular ion peak (M+1) 144.0.

(2) Preparation of intermediate 3: in a 3 L reaction flask, DCM (dichloromethane) (500 mL), intermediate 2 (39 g, 217 mmol), 1148-11-4 (N-benzyloxycarbonyl-L-proline) (54 g, 217 mmol) and Et₃N (87.7 g, 868 mmol) were added successively. Under nitrogen protection, the reaction solution was cooled to 0° C. and HATU (2-(7-azobenzotriazole)-tetramethylurea hexafluorophosphate) (98.8 g, 260 mmol) was added in batches. The reaction solution was naturally warmed to room temperature, and the reaction was carried out for 14 hours under stirring. After the reaction was completed, HCl (400 mL, 0.5 N H₂O) was added, the obtained mixture was filtered through diatomite and was extracted, the organic phase was washed with NaHCO₃ (5%) and saturated saline solution, dried over Na₂SO₄ and concentrated, then passed through column (PE (polyethylene): EA (ethyl acrylate)=1:1) to obtain intermediate 3 (12.7 g, yield: 14.7%) as a white solid. LCMS showed a molecular ion peak (M+1) 375.0.

(3) Preparation of intermediate 4: in a 250 mL three neck reaction flask, ACN (acetonitrile) (48 mL) and POCl₃ (16 mL, 175 mol) were added, the obtained solution was preheated to 80° C. Intermediate 3 (8 g, 21.3 mmol) was dissolved in ACN (32 mL) and then the obtained solution was quickly added to the preheated solution. The reaction solution was reacted at 80° C. for 3.5 hours. After cooling to room temperature, the reaction solution was slowly poured into a solution of NH₃.H₂O in ice water. NH₃.H₂O was added continuously to adjust pH=8-9. The aqueous phase was extracted with ethyl acetate for three times. The organic phase was washed with saturated saline solution, dried over Na₂SO₄ and concentrated to obtain intermediate 4 as a solid which was directly used in the reaction of the next step. LCMS showed a molecular ion peak (M+1) 357.0.

(4) Preparation of intermediate 5: in a 100 mL reaction flask, DMF (N,N-dimethylformamide) (20 mL), intermediate 4 (21.3 mmol) and NBS (n-bromosuccinimide) (3.791 g, 21.3 mmol) were added successively. The reaction solution was stirred at atmospheric temperature for 12 hours and was purified by reversed phase column to obtain intermediate 5 (6.67 g, the yield of two steps: 72%) as a white solid. LCMS showed a molecular ion peak (M+1) 434.9.

(5) Preparation of intermediate 6: in a 250 mL sealed tube, intermediate 5 (6 g, 13.8 mmol), IPA (isopropanol) (90 mL) and NH₃.H₂O (135 mL) were added successively. The reaction solution was reacted at 90° C. for 14 hours, concentrated and purified by reversed phase column to obtain intermediate 6 (5 g, yield: 87%) as a white solid. LCMS showed a molecular ion peak (M+1) 415.9.

(6) Preparation of intermediate 8: in a 1 L reaction flask, SOCl₂ (thionyl dichloride) (100 mL) and compound 7a (36.9 g, 300 mmol) were added successively. Under nitrogen protection, the reaction solution was stirred at 80° C. for 4 hours, cooled and then concentrated. DCM (dichloromethane) (400 mL) was added, cooled to 10° C. and Et₃N (121.1 g, 1200 mmol) was added slowly under nitrogen protection.

The obtained system was cooled to 0° C., a solution of 106-40-1 (p-bromoaniline) (51.6 g, 300 mmol) in DCM (100 mL) was added dropwise. The temperature was naturally increased to room temperature and the obtained system continued to react for 14 hours and was concentrated and separated by rapid column chromatography to obtain intermediate 8 (33.39 g, yield: 40%) as a grey solid. LCMS showed a molecular ion peak (M+1) 277.0.

(7) Preparation of intermediate 9: in a 1 L reaction flask, intermediate 8 (13.8 g, 50 mmol), bis(pinacolato)diboron (13.97 g, 55 mmol), KOAc (potassium acetate) (14.7 g, 150 mmol), Pd(dppf)Cl$_2$ ([1,1'-bis(diphenylphosphino)ferrocene]dichloropalladium) (1.5 g) and dioxane (250 mL) were added successively. The reaction solution was reacted at 100° C. for 14 hours under argon protection. The reaction solution was cooled, then concentrated and separated by rapid column chromatography to obtain intermediate 9 (10.93 g, yield: 68%) as a white solid. LCMS showed a molecular ion peak (M+1) 325.0.

(8) Preparation of intermediate 10: in a 30 mL microwave reaction tube, intermediate 9 (970 mg, 3 mmol), intermediate 6 (625 mg, 1.5 mmol), Pd(dppf)Cl$_2$ (200 mg), K$_2$CO$_3$ (2.2 mL 2.0 N, 4.4 mmol) and dioxane (7 mL) were added successively. The reaction solution was purged with nitrogen and was microwave-heated to 140° C. to be reacted for 30 minutes. The reaction solution was cooled and was then extracted with EA (ethyl acrylate) for three times. The organic phase was concentrated and was then subjected to rapid column chromatography and purification by reverse phase column to obtain intermediate 10 (500 mg, yield: 62%) as a brown solid. LCMS showed a molecular ion peak (M+1) 534.0.

(9) Preparation of intermediate 11: in a 50 mL reaction flask, intermediate 10 (500 mg, 0.94 mmol) and a solution of HBr in CH$_3$COOH (7 mL, mass concentration of HBr: 33%) was added successively. The reaction solution was stirred at atmospheric temperature for 4 hours. Water was added, the obtained system was extracted three times with DCM (dichloromethane). The aqueous phase was adjusted to pH=8-9 with solid Na$_2$CO$_3$ and was extracted with DCM for three times. The organic phase was washed with saturated saline water, dried over Na$_2$SO$_4$, concentrated then purified by traverse phase column to obtain intermediate 11 (100 mg. yield: 27%) as a white solid. LCMS showed a molecular ion peak (M+1) 400.0.

(10) Preparation of the compound of formula Ia: in a 25 mL reaction flask, DCM (dichloromethane) (5 mL), intermediate 11 (90 mg, 0.23 mmol), 590-93-2 (2-butynoic acid) (19.3 mg, 0.23 mmol), Et$_3$N (68 mg, 0.68 mmol) and HATU (2-(7-azobenzotriazole)-tetramethylurea hexafluorophosphate) (87.5 mg, 0.23 mmol) were added successively. The reaction solution was stirred at atmospheric temperature for 30 minutes under nitrogen protection. The reaction solution was concentrated, purified by big plate and reverse phase column to obtain compound of formula Ia (47 mg, yield: 45%) as a white solid.

LCMS showed a molecular ion peak (M+1) 466.3.

The obtained target product Ia was subjected to hydrogen nuclear magnetic resonance $^1$H-NMR (400 MHz, d-DMSO) and mass spectrometry, and the results were as follows: absorption peaks in $^1$H-NMR spectrum: δ=10.80 (1H, CONH), 8.78-8.77 (1H, ArH), 8.20-8.18 (1H, ArH), 8.11-8.06 (3H, ArH), 7.81-7.74 (1H, ArH), 7.71-7.69 (1H, ArH), 7.60-7.59 (2H, ArH), 7.11-7.06 (1H, ArH), 6.09-6.03 (2H, NH2), 5.71-5.45 (1H, a-H), 3.83-3.78, 3.61-3.55 (2H, d-H), 2.42-1.93, 1.63 (7H, b-H, c-H, —CH$_3$).

m/z [MH]$^+$: 466.3. It was calculated that the product has the molecular formula C$_{26}$H$_{23}$N$_7$O$_2$, and the exact molecular mass (exact mass) of the product was 465.19.

Example 2

The compound of formula Ib, i.e, the above (II-1), having a chemical structure as shown below:

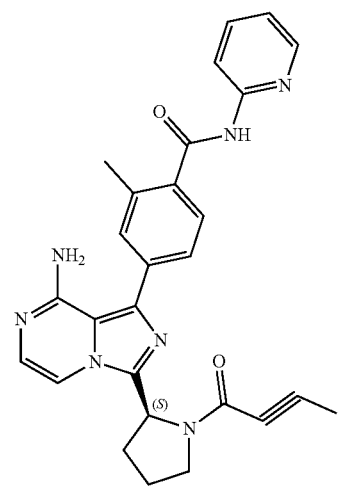

the compound of formula Ib can be obtained by the following synthesis route:

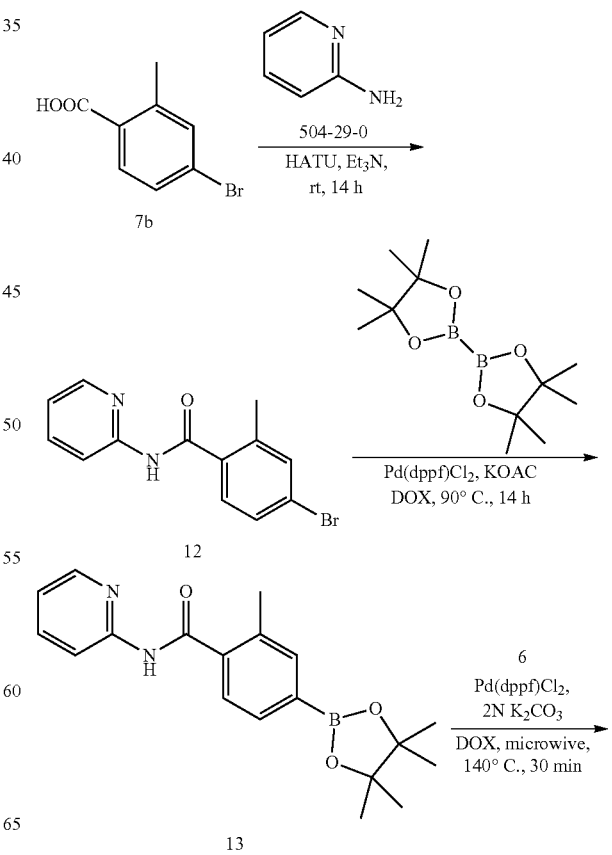

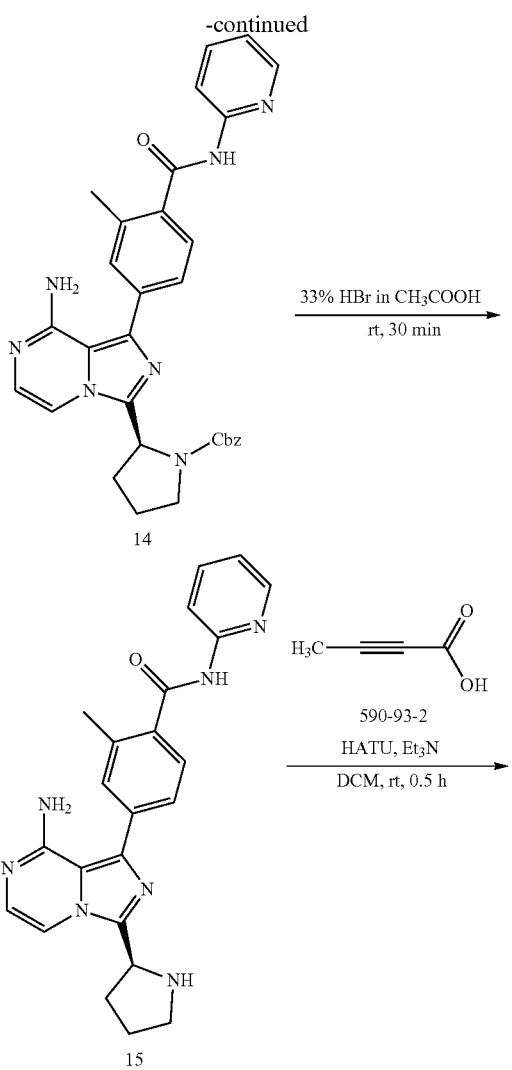

(19 g, 50 mmol) were added successively. The obtained system was stirred at atmospheric temperature for 20 minutes under argon protection. A solution of 504-29-0 (2-aminopyridine) (4.5 g, 47.9 mmol) in THF (100 mL) was added slowly to the above solution, the obtained system was stirred under atmospheric temperature for 14 hours and was concentrated, subjected to rapid column chromatography and reverse phase column purification to obtain intermediate 12 (2 g, yield: 14.2%) as a white solid. LCMS showed a molecular ion peak (M+1) 290.9.

(2) Preparation of intermediate 13: the method for the synthesis of intermediate 13 was similar to the method for the synthesis of intermediate 9, intermediate 13 was obtained (1.3 g, yield: 56%) as a yellow solid. LCMS showed a molecular ion peak (M+1) 339.1.

(3) Preparation of intermediate 14: the method for the synthesis of intermediate 14 was similar to the method for the synthesis of intermediate 10, intermediate 14 was obtained (513 mg, yield: 67%) as a yellow solid. LCMS showed a molecular ion peak (M+1) 548.0.

(4) Preparation of intermediate 15: the method for the synthesis of intermediate 15 was similar to the method for the synthesis of intermediate 11, intermediate 15 was obtained (210 mg, yield: 69.6%) as a yellow solid. LCMS showed a molecular ion peak (M+1) 414.0.

(5) Preparation of the compound of formula Ib: the method for the synthesis of the compound of formula Ib was similar to the method for the synthesis of the compound of formula Ia, the compound of formula Ib was obtained (35 mg, yield: 18.2%) as a white solid.

The obtained target product Ib was subjected to hydrogen nuclear magnetic resonance $^1$H-NMR (400 MHz, d-DMSO) and mass spectrometry, and the results were as follows: absorption peaks in $^1$H-NMR spectrum: δ=10.79 (1H, CONH), 8.37-8.36 (1H, ArH), 8.23-8.21 (1H, ArH), 7.87-7.77 (2H, ArH), 7.62-7.60 (1H, ArH), 7.50-7.45 (2H, ArH), 7.18-7.09 (2H, ArH), 6.14-6.09 (2H, NH2), 5.72-5.46 (1H, a-H), 3.84-3.80, 3.62-3.56 (2H, d-H), 2.47 (3H, PhCH3), 2.42-1.92, 1.63 (7H, b-H, c-H, —CH3).

m/z [MH]$^+$: 480.2. It was calculated that the product has the molecular formula $C_{27}H_{25}N_7O_2$, and the exact molecular mass (exact mass) of the product was 479.21.

Example 3

The compound of formula Ic, (i.e, the above 1-2), having a chemical structure as shown below:

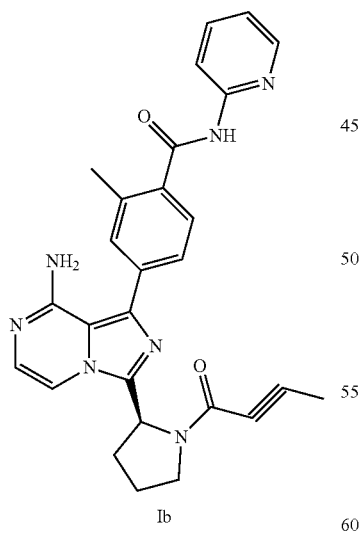

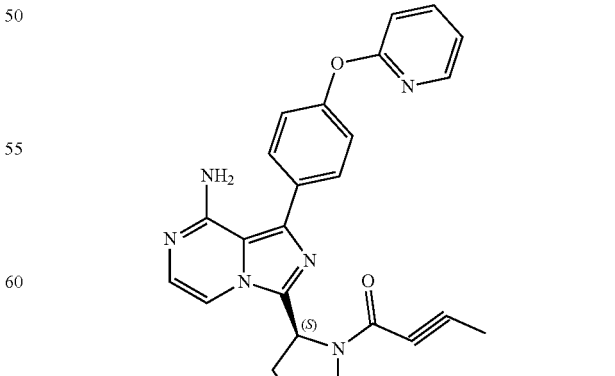

the preparation method of the compound of formula Ib specifically comprises the following steps:
(1) preparation of intermediate 12: in a 500 mL reaction flask, THF (tetrahydrofuran) (100 mL), compound 7a (10.75 g, 50 mmol), Et$_3$N (15.15 g, 150 mmol) and HATU (2-(7-azobenzotriazole)-tetramethylurea hexafluorophosphate)

the compound of formula Ic can be obtained by the following synthesis route:

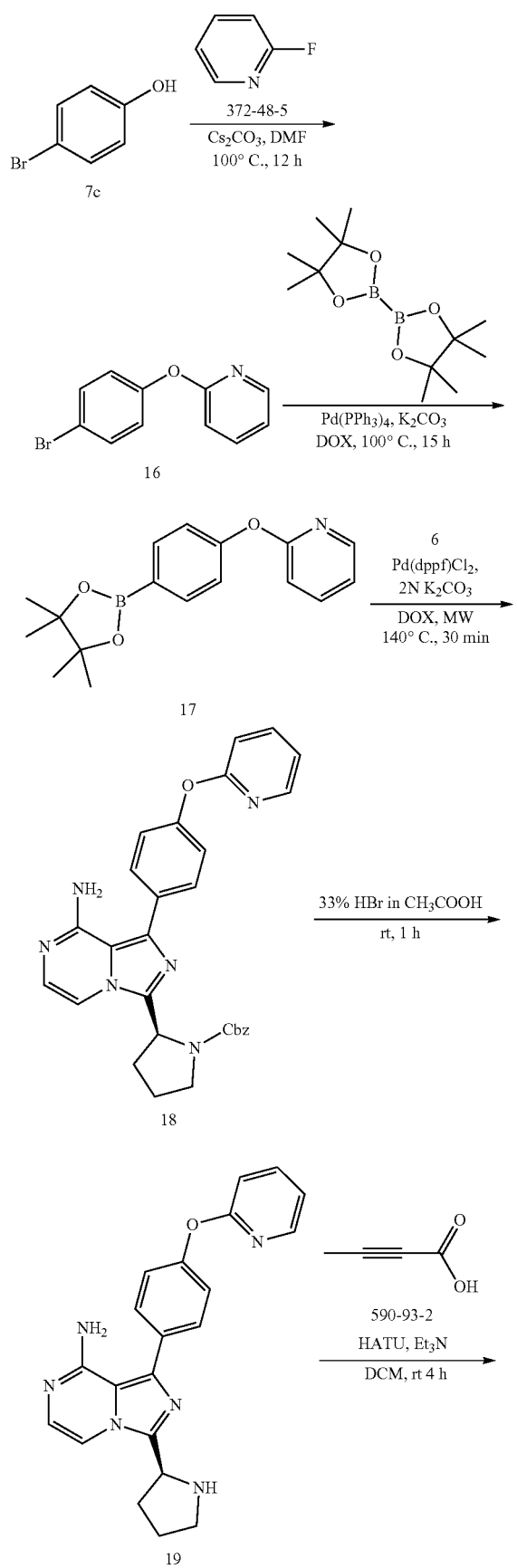

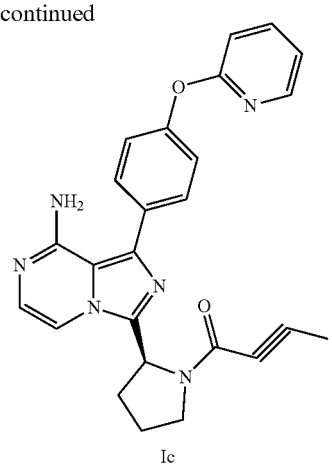

Ic the preparation method of the compound of formula Ic specifically comprises the following steps:

(1) preparation of intermediate 16: in a 50 mL reaction flask, DMF (N,N-dimethylformamide) (20 mL), compound 7c (1.71 g, 10 mmol), 372-48-5 (2-fluoropyridine) (970 mg, 10 mmol) and Cs$_2$CO$_3$ (6.52 g, 20 mmol) were added successively. The reaction solution was reacted under heating and argon protection for 12 hours. The reaction solution was cooled, then H$_2$O was added and the obtained system was extracted with ethyl acetate for three times. The organic phase was washed with saturated saline water, dried over Na$_2$SO$_4$ and concentrated to obtain intermediate 16 (1.8 g) which was directly used in the reaction of the next step. LCMS showed a molecular ion peak (M+1) 250.0.

(2) Preparation of intermediate 17: in a 50 mL reaction flask, intermediate 16 (1.8 g, 7 mmol), bis(pinacolato)diboron (3.556 g, 14 mmol), K$_2$CO$_3$ (2.898 g, 21 mmol), Pd(PPh$_3$)$_4$ (tetrakis(triphenylphosphine)palladium) (500 mg) and dioxane (10 mL) were added successively. The reaction solution was reacted at 100° C. for 15 hours under argon protection. The reaction solution was cooled, then was concentrated and separated by rapid column chromatography to obtain intermediate 17 (2 g) as a brown solid. LCMS showed a molecular ion peak (M+1) 298.1.

(3) Preparation of intermediate 18: in a 30 mL microwave reaction tube, intermediate 17 (2 g, 6.7 mmol), intermediate 6 (625 mg, 1.5 mmol), Pd(dppf)Cl$_2$ ([1,1'-bis(diphenylphosphino)ferrocene]dichloropalladium) (300 mg), K$_2$CO$_3$ (2 mL 2.0 N, 4 mmol) and dioxane (8 mL) were added successively. The reaction solution was purged with nitrogen and was microwave-heated to 140° C. to be reacted for 30 minutes. The reaction solution was cooled, then concentrated and purified by reverse phase column to obtain intermediate 18 (220 mg, yield: 28.9%) as a white solid. LCMS showed a molecular ion peak (M+1) 507.1.

(4) Preparation of intermediate 19: in a 50 mL reaction flask, intermediate 18 (220 mg, 0.43 mmol) and a solution of HBr in CH$_3$COOH (8 mL, mass concentration of HBr: 33%) was added successively. The reaction solution was stirred at atmospheric temperature for 4 hours. Water was added, the obtained system was extracted three times with DCM (dichloromethane). The aqueous phase was adjusted to pH=8-9 with solid Na$_2$CO$_3$ and was extracted with DCM for three times. The organic phase was washed with saturated saline water, dried over Na₂SO₄, concentrated then purified by traverse phase column to obtain intermediate 19 (120 mg. yield: 75%) as a white solid. LCMS showed a molecular ion peak (M+1) 373.1.

(5) Preparation of the compound of formula Ic: in a 25 mL reaction flask, DCM (dichloromethane) (5 mL), intermediate 23 (120 mg, 0.32 mmol), 590-93-2 (2-butynoic acid) (27 mg, 0.32 mmol), Et₃N (96 mg, 0.96 mmol) and HATU (2-(7-azobenzotriazole)-tetramethylurea hexafluorophosphate) (152 mg, 0.4 mmol) were added successively. The reaction solution was stirred at atmospheric temperature for 4 hours under nitrogen protection. The reaction solution was concentrated, purified by reverse phase column to obtain compound of formula Ic (59 mg, yield: 42%) as a white solid.

The obtained target product Ic was subjected to hydrogen nuclear magnetic resonance ¹H-NMR (400 MHz, d-DMSO) and mass spectrometry, and the results were as follows:

absorption peaks in ¹H-NMR spectrum: δ=8.20-8.19 (1H, ArH), 7.90-7.87 (1H, ArH), 7.83-7.75 (1H, ArH), 7.64-7.60 (2H, ArH), 7.26-7.24 (2H, ArH), 7.18-7.15 (1H, ArH), 7.11-7.17 (2H, ArH), 6.13-6.07 (2H, NH2), 5.71-5.45 (1H, a-H), 3.82-3.79 (1H, d-H), 3.61-3.54 (1H, d-H), 2.43-1.92, 1.63 (7H, b-H, c-H, —CH₃).

m/z [MH]⁺: 439.2. It was calculated that the product has the molecular formula $C_{25}H_{22}N_6O_2$, and the exact molecular mass (exact mass) of the product was 438.18.

Example 4

The compound of formula Id (i.e, the above I-1), having a chemical structure as shown below:

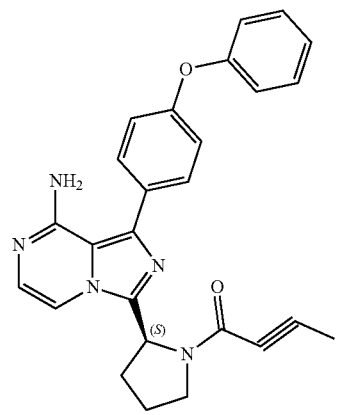

the compound of formula Id can be obtained by the following synthesis route:

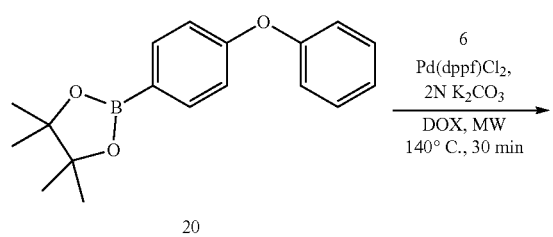

the preparation method of the compound of formula Id specifically comprises the following steps:

(1) preparation of intermediate 21: the method for the synthesis of intermediate 21 was similar to the method for the synthesis of intermediate 18, intermediate 21 was obtained (200 mg, yield: 46.4%) as a white solid. LCMS showed a molecular ion peak (M+1) 506.2.

(2) Preparation of intermediate 22: the method for the synthesis of intermediate 22 was similar to the method for the synthesis of intermediate 19, intermediate 22 was obtained (116 mg, yield: 78%) as a white solid. LCMS showed a molecular ion peak (M+1) 372.1.

(3) Preparation of the compound of formula Id: the method for the synthesis of the compound of formula Id was similar

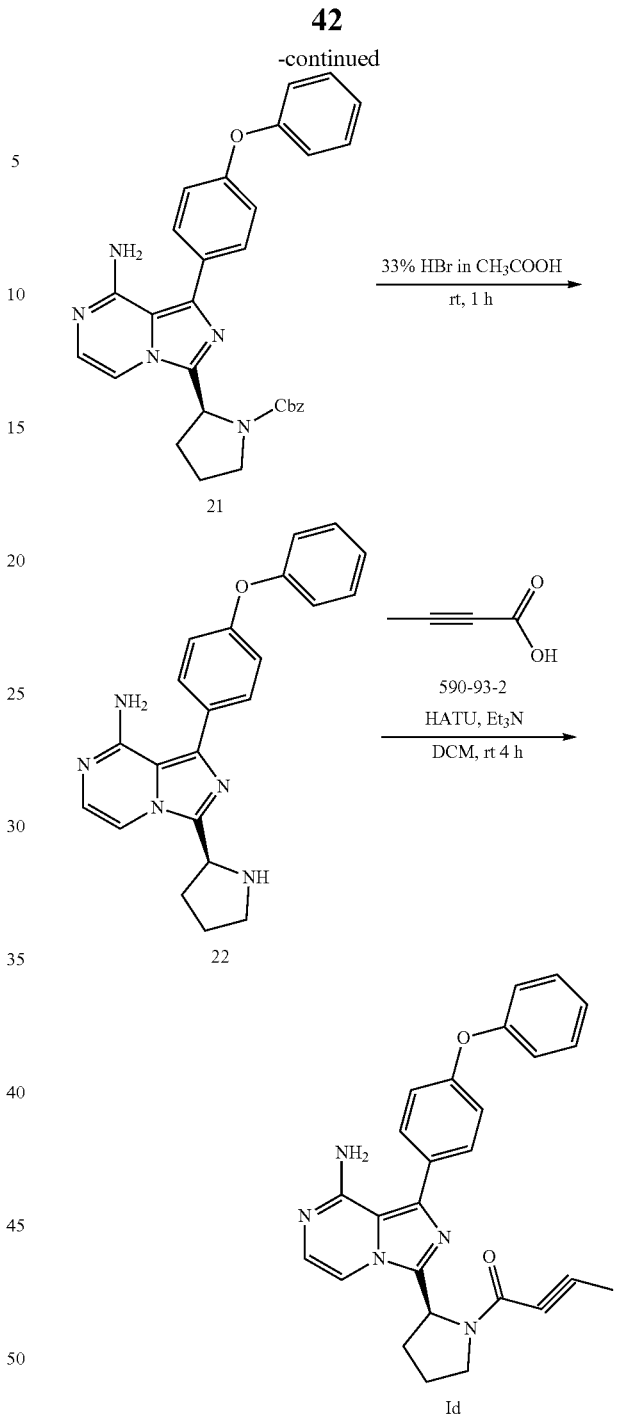

to the method for the synthesis of the compound of formula Ic, the compound of formula Id was obtained (116 mg, yield: 43.6%) as a white solid.

The obtained target product Ib was subjected to hydrogen nuclear magnetic resonance $^1$H-NMR (400 MHz, d-DMSO) and mass spectrometry, and the results were as follows:

absorption peaks in $^1$H-NMR spectrum: δ=7.82-7.34 (1H, ArH), 7.61-7.57 (2H, ArH), 7.44-7.40 (2H, ArH), 7.19-7.15 (1H, ArH), 7.13-7.05 (5H, ArH), 6.11-6.05 (2H, NH2), 5.70-5.44 (1H, a-H), 3.82-3.79, 3.61-3.55 (2H, d-H), 2.43-1.94, 1.62 (7H, b-H, c-H, —CH3).

m/z [MH]$^+$: 438.2. It was calculated that the product has the molecular formula $C_{26}H_{23}N_5O_2$, and the exact molecular mass (exact mass) of the product was 437.19.

Pharmacology Tests

To screen compounds against kinases:

Experiment Method

The semi-inhibitory concentration $IC_{50}$ of the compound (the concentration of the compound required to inhibit the enzyme activity to 50%) is determined by mixing a fixed enzyme with a specific substrate and different concentrations of the test compounds. The test method used was the Caliper Mobility Shift Assay, the kinases to be tested are BTK, ITK, TEC, EGFR, HER2, HER4, JAK3, HCK, LYN, SRC and SYK. The standard reference compound used was staurosporine.

Test Results

The results of experiments on the inhibitions of BTK enzyme activity by the target compounds (Ia, Ib, Ic and Id) were summarized in Table 1. The results showed that the target compounds (Ib and Id) had very strong inhibiting effects on BTK kinase, and the compounds of formula Ia and Ic also had strong inhibiting effects on BTK kinase.

The results of experiments on the inhibitions of ITK, TEC, EGFR, HER2, HER4, JAK3, HCK, LYN, SRC and SYK enzyme activities by the target compound Id were summarized in Table 2. The results showed that the selective inhibiting activity of the target compound Id was good. This selective inhibiting effect has important values for the treatment of diseases such as rheumatoid arthritis, B cell lymphoma, leukemia, multiple myeloma, allergies, asthma, multiple sclerosis, type I diabetes and systemic lupus erythematosus. The tests of other compounds of the present invention also have similar results.

TABLE 1

| Compound | Inhibition on kinase activity ($IC_{50}$, nM) |
|---|---|
| Compound of formula Ia | 415 |
| Compound of formula Ib | 50 |
| Compound of formula Ic | 577 |
| Compound of formula Id | 4.8 |
| Ibrutinib | 1.5 |
| Acalabrutinib | 11 |

TABLE 2

| | Inhibition on kinase activity ($IC_{50}$, nM) | | |
|---|---|---|---|
| Kinase | Compound of formula Id | Acalabrutinib | Ibrutinib |
| ITK | >1000 | >1000 | 787 |
| TEC | 40 | 37 | 7 |
| EGFR | >1000 | >1000 | 10 |
| HER2 | >1000 | >1000 | 63 |
| HER4 | >1000 | >1000 | 16 |
| JAK3 | >1000 | >1000 | 233 |

TABLE 2-continued

| | Inhibition on kinase activity ($IC_{50}$, nM) | | |
|---|---|---|---|
| Kinase | Compound of formula Id | Acalabrutinib | Ibrutinib |
| HCK | >1000 | >1000 | 1267 |
| LYN | >1000 | >1000 | 187 |
| SRC | >1000 | >1000 | 610 |
| SYK | >1000 | >1000 | >1000 |

Assessments of Pharmacokinetic Properties:

1. Experiment Method

Experiment animals: CD-1 mouse, males and females; body weight: 20-25 g;

Preparation of test samples: the target compound was formulated into 0.2 mg/mL (for intravenous administration) and 1.0 mg/mL (for oral administration) for later use. Route of administration: oral/intravenous. Dosage and dosing frequency: 2 mL/kg (intravenous) or 5 mL/kg (oral), single administration.

Sample collection: blood samples were collected at the following time points: 5 minutes, 15 minutes, 30 minutes, 1 hours, 2 hours, 4 hours, 8 hours and 24 hours after administration.

2. Sample Analysis and Results

Sample analysis: The collected samples were tested using the LC-MS/MS method. The model of the instrument used was API4000.

Pharmacokinetic data analysis: the obtained plasma concentration data were fitted and calculated according to the non-compartmental model method using WinNolin. Some results are summarized in Table 3.

TABLE 3

| Dosage (mg/kg) | Route of administration | Pharmacokinetic parameters (unit) | Compound of formula Id |
|---|---|---|---|
| 3 | Intravenous injection | CL (L/hr/kg) | 4.62 |
| | | Vss (L/kg) | 1.30 |
| | | Terminal $t_{1/2}$ (hr) | 0.286 |
| | | $AUC_{last}$ (hr*ng/mL) | 661 |
| | | $MRT_{INF}$ (hr) | 0.297 |
| 15 | Oral | $T_{max}$ (hr) | 0.25 |
| | | $C_{max}$ (ng/mL) | 848 |
| | | Terminal $t_{1/2}$ (hr) | 1.64 |
| | | $AUC_{last}$ (hr*ng/mL) | 1878 |
| | | F (%) | 56.4 |

In Table 3, CL: clearance. $V_{SS}$: apparent volume of distribution at steady state. Terminal $t_{1/2}$: half life. $AUC_{last}$: area under the curve. $MRT_{INF}$: average residence time. $T_{max}$: peak time. $C_{max}$: peak concentration. F: bioavailability, refers to the fraction of oral dosage actually reaching the blood circulation.

The test results showed that the compound of the present invention has good pharmacokinetic characteristics and a short half life, which can reduce risks of immune side reactions that may be caused by inhibition of BTK. At the same time, $T_{max}$ is small, and the peak plasma concentration can be reached very quickly, so that the drug took effect quickly.

In addition, in vitro liver microsomal metabolism of the compounds of the present invention was also tested. The test compound was co-incubated with NADPH and mouse or human liver microsomes in a 37° C. water bath pot, a reaction was initiated by adding the test compound. 20 of the incubated sample was taken at different time points (0, 10, 20, 40 and 60 minutes) and transferred to acetonitrile containing an internal standard. After proteins were precipitated, the supernatant was obtained by centrifugation. The test compound in the supernatant was analyzed by the LC-MS/MS method. The intrinsic clearance in vitro was calculated according to the elimination half life of the test compound in the incubation system. Midazolam was subjected to parallel incubation as a positive control. The $T_{1/2}$ of the compound of formula Id in mouse and human liver microsomes was 8.26 minutes and 3.13 minutes, respectively, and the intrinsic clearance ($CL_{int}$) was 660.83 mL/min/kg and 555.11 mL/min/kg, respectively. In the same test, acalabrutinib had a $T_{1/2}$ of 23.32 minutes in mouse liver microsome and a $T_{1/2}$ of 11.88 minutes in human liver microsome, respectively, and the intrinsic clearances were 234.03 mL/min/kg and 146.3 mL/min/kg, respectively. The results of these tests showed that the compound of formula Id was metabolized faster than acalabrutinib in vivo, thereby predicting that the risks of immune side effects caused by the inhibition of BTK for compound of formula Id were lower than acalabrutinib. Tests of the other compounds of the present invention also had similar results.

The above examples are merely representative examples. As can be seen from the above examples, the compounds of the present invention are ideal highly efficient selective BTK kinase inhibitors and are expected to be used in the treatment or prevention of diseases such as rheumatoid arthritis, B cell lymphoma, leukemia, multiple myeloma, allergies, asthma, multiple sclerosis, type I diabetes and systemic lupus erythematosus and achieve very good results. They can also be combined with different types of medicinal salts to form oral preparations (tablets or capsules, etc.). Tablets or capsules made with the compounds of the present invention can be taken one or more times a day. The compounds of the present invention can also be combined with other drugs to prepare compound preparations.

The above examples are only provided to illustrate the technical concept and the features of the present invention with the purposes of enabling a person skilled in the art to understand the contents of the present invention and to implement the present invention accordingly, the protection scope of the present invention shall not be limited thereby. Equivalent changes or modifications made in accordance with the spirit of the present invention shall be included within the protection scope of the present invention.

The invention claimed is:

1. An imidazopyrazinamine phenyl derivative having a structure represented by general formula (I), a pharmaceutically acceptable salt or hydrate thereof,

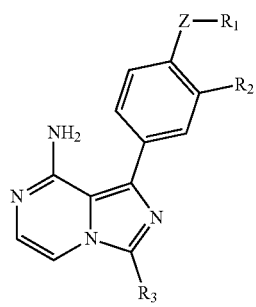
(I)

wherein: Z is selected from NH, C=O or O;
R$_1$ is a benzene ring, a six-membered heteroaromatic ring having 1 or 2 nitrogens, which is optionally substituted with 0-2 C1-C4 alkyls;
R$_2$ is H, C1-C4 alkyl or halogen;
R$_3$ is

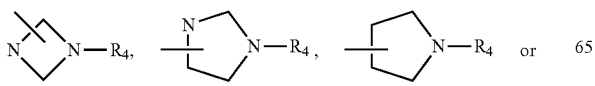

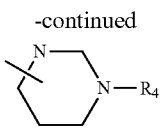

wherein R$_4$ is C(O)C≡CR$_5$ or C(O)CH=CHR$_5$, and R$_5$ is H or C1-C4 alkyl.

2. The imidazopyrazinamine phenyl derivative according to claim 1, a pharmaceutically acceptable salt or hydrate thereof, wherein R$_2$ is H, methyl, ethyl, n-propyl, isopropyl, n-butyl, isobutyl, sec-butyl or tert-butyl.

3. The imidazopyrazinamine phenyl derivative according to claim 1, a pharmaceutically acceptable salt or hydrate thereof, wherein R$_3$ is

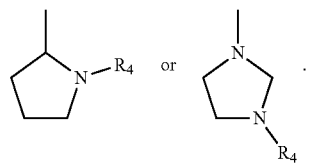

4. The imidazopyrazinamine phenyl derivative according to claim 1, a pharmaceutically acceptable salt or hydrate thereof, wherein R$_5$ is H, methyl, ethyl, n-propyl, isopropyl, n-butyl, isobutyl, sec-butyl or tert-butyl.

5. The imidazopyrazinamine phenyl derivative according to claim 1, a pharmaceutically acceptable salt or hydrate thereof, wherein the imidazopyrazinamine phenyl derivative is one of the compounds represented by the following structural formulas:

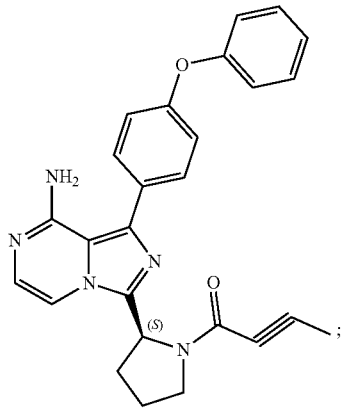
(I-1)

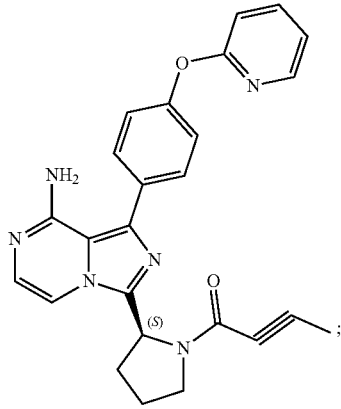
(I-2)

(I-3)
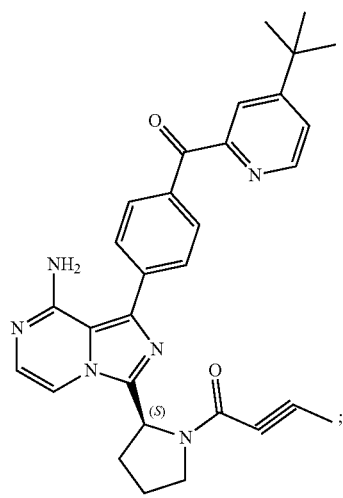
(I-4)
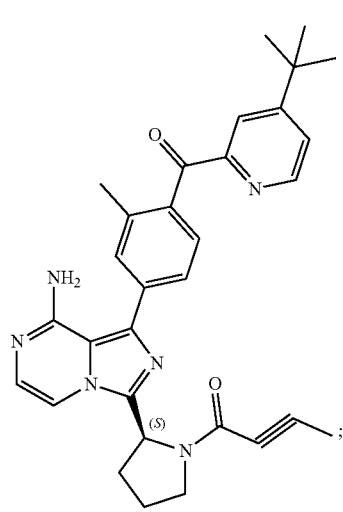
(I-5)
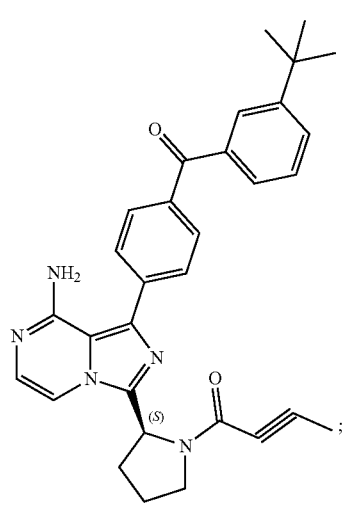
(I-6)
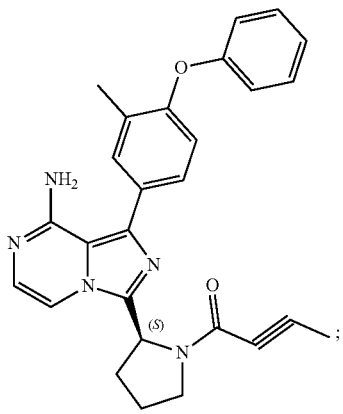
(I-7)
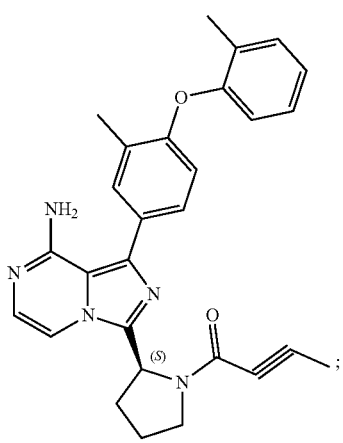
(I-8)
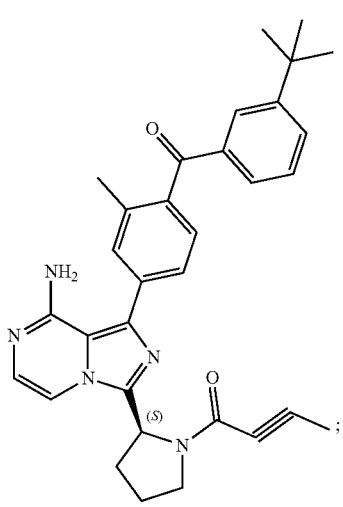

-continued
(I-9)
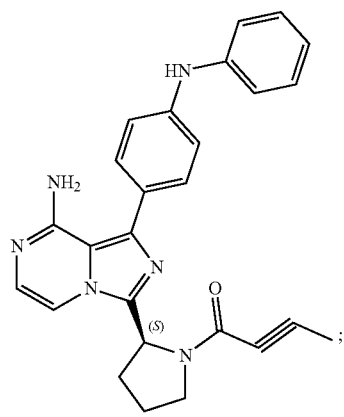
(I-10)
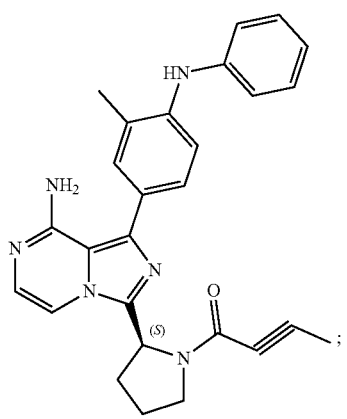
(I-11)
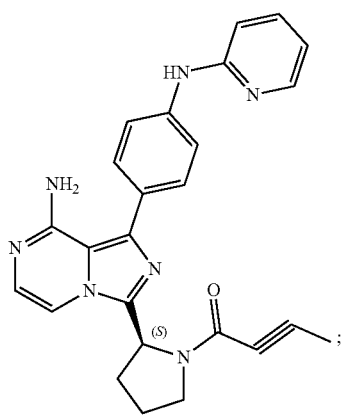
(I-12)
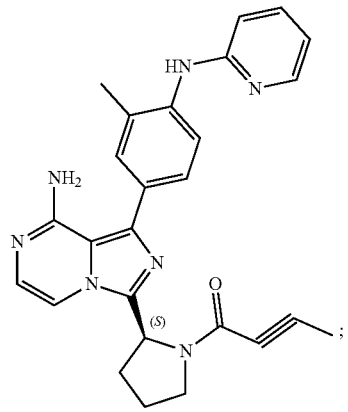
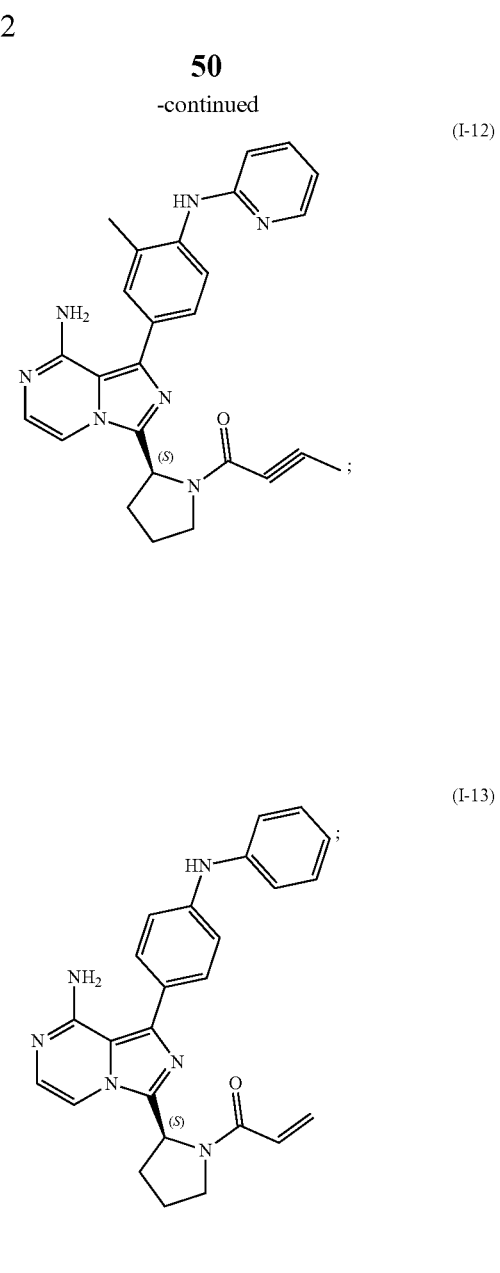

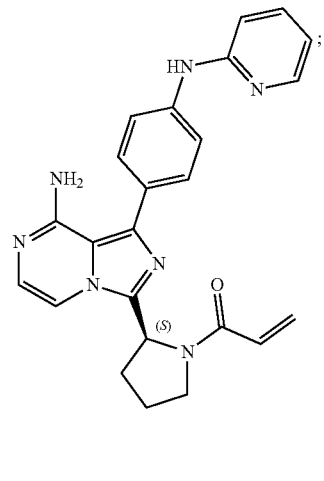
(I-15)
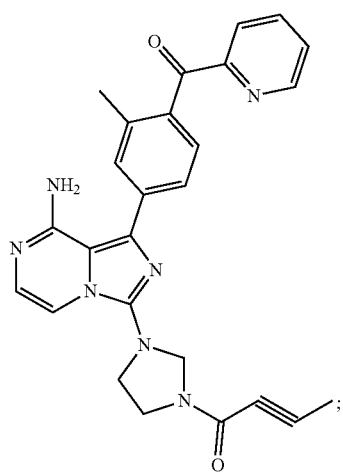
(I-18)
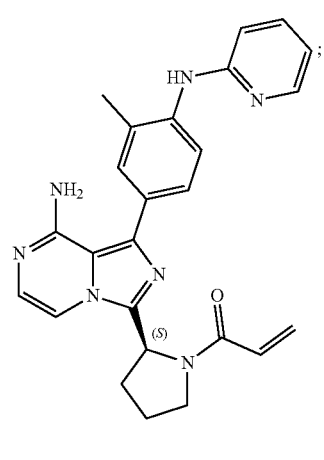
(I-16)
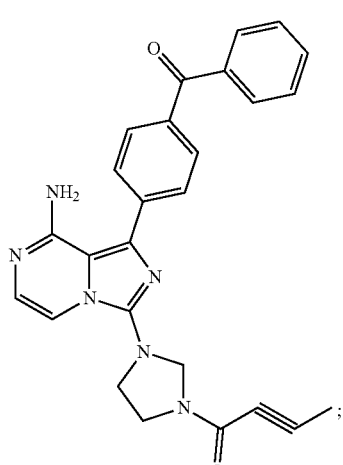
(I-19)
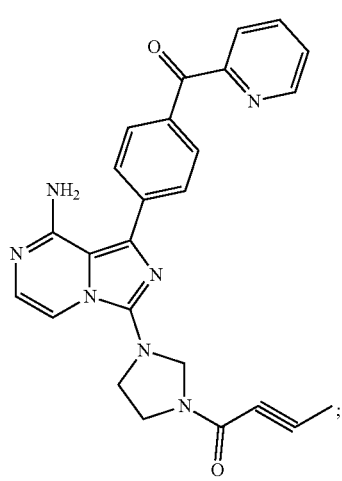
(I-17)
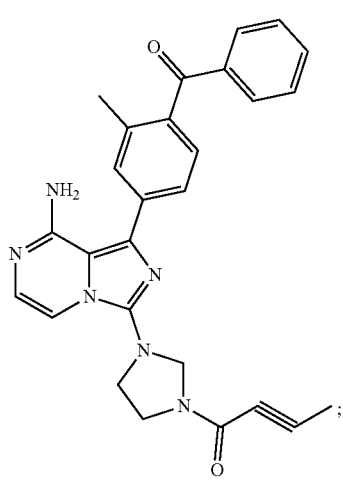
(I-20)

(I-21)
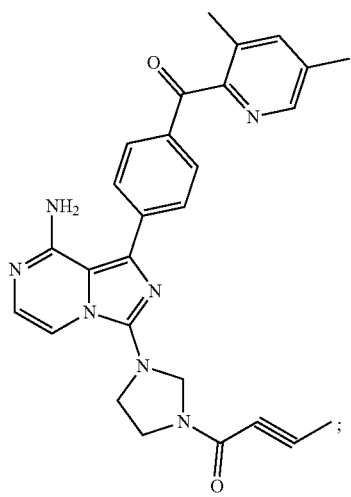
(I-22)
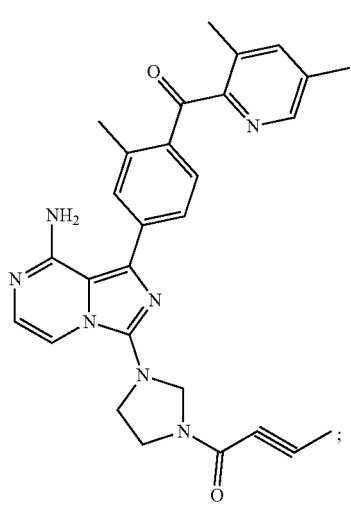
(I-23)
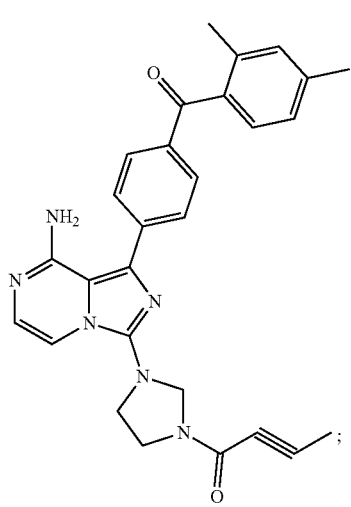
(I-24)
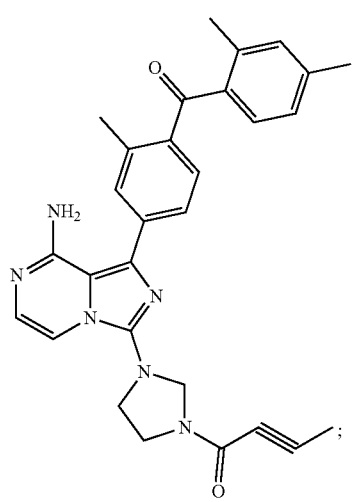
(I-25)
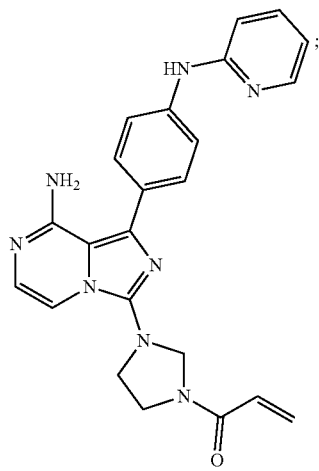
(I-26)
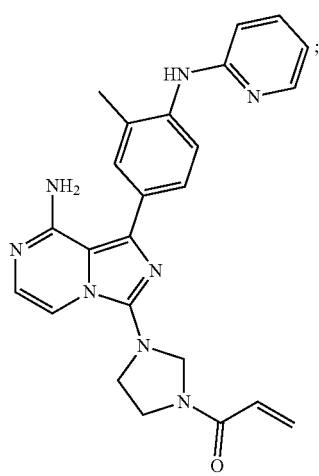

(I-27)
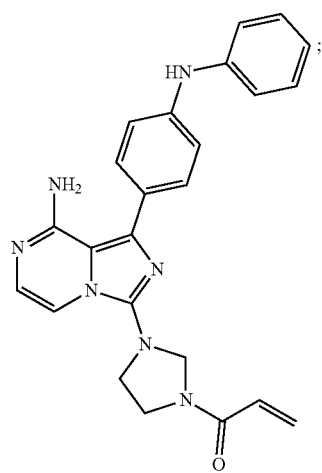
(I-28)
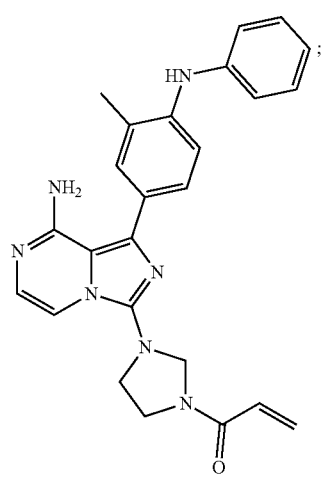
(I-29)
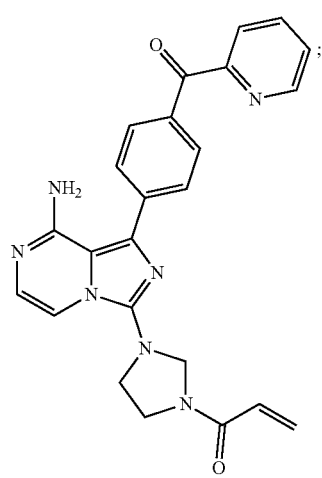
(I-30)
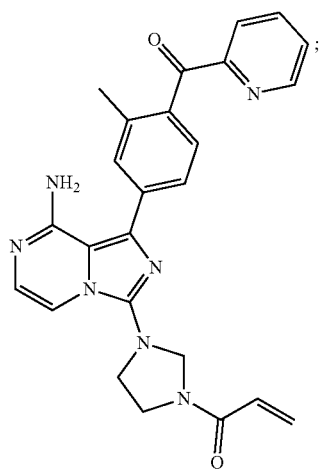
(I-31)
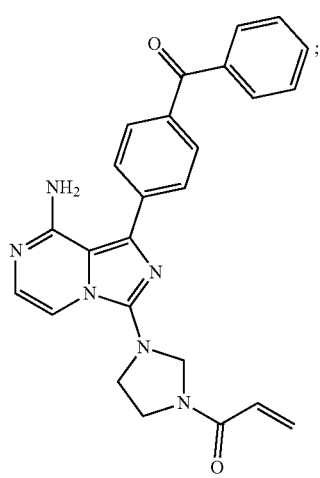
(I-32)
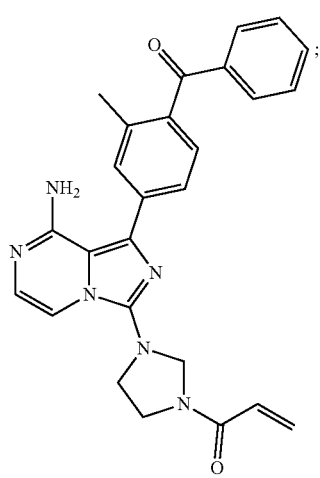

-continued (I-33)
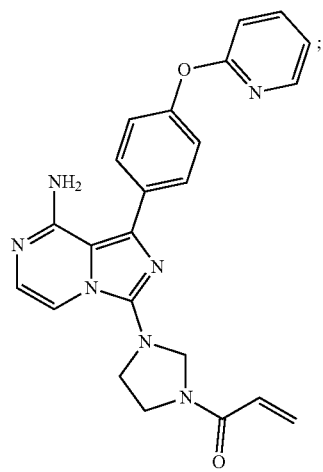

(I-34)
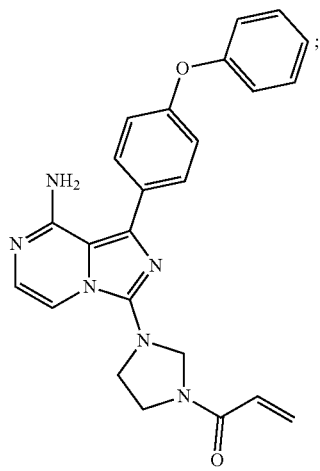

-continued (I-35)
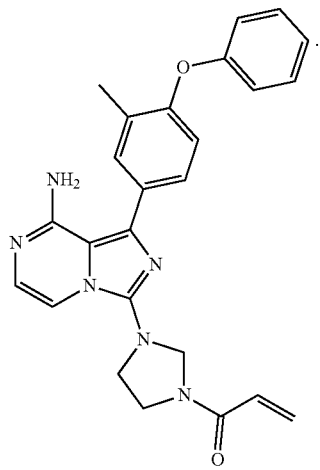

(I-36)
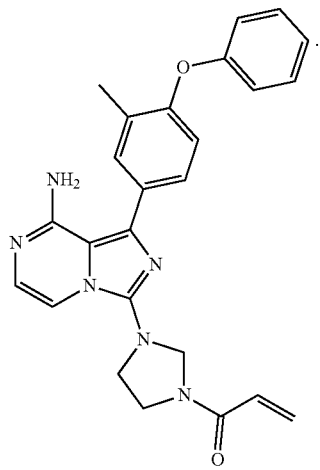

6. A method for treating an indication/disease associated with BTK functions, the method comprising administering the imidazopyrazinamine phenyl derivative having a structure represented by general formula (I) according to claim 1, a pharmaceutically acceptable salt or hydrate thereof, wherein the indication/disease associated with BTK functions is B cell lymphoma.

* * * * *